(12) United States Patent
Clink et al.

(10) Patent No.: US 8,875,438 B2
(45) Date of Patent: Nov. 4, 2014

(54) METHOD OF PESTICIDE TREATMENT OF SOIL ADJACENT STRUCTURES

(75) Inventors: James H. Clink, Ballwin, MO (US); Richard A. Warriner, Wake Forest, NC (US)

(73) Assignee: BASF Agro B.V. (CH)

(*) Notice: Subject to any disclaimer, the term of this patent is extended or adjusted under 35 U.S.C. 154(b) by 290 days.

(21) Appl. No.: 13/033,457

(22) Filed: Feb. 23, 2011

(65) Prior Publication Data

US 2011/0203162 A1 Aug. 25, 2011

Related U.S. Application Data

(60) Provisional application No. 61/307,178, filed on Feb. 23, 2010, provisional application No. 61/307,183, filed on Feb. 23, 2010.

(51) Int. Cl.
| | | |
|---|---|---|
| *A01M 1/20* | (2006.01) | |
| *A01C 23/02* | (2006.01) | |
| *A01M 17/00* | (2006.01) | |
| *A01M 21/04* | (2006.01) | |
| *A01N 25/02* | (2006.01) | |

(52) U.S. Cl.
CPC ............. *A01N 25/02* (2013.01); *A01C 23/028* (2013.01); *A01M 17/002* (2013.01); *A01M 21/043* (2013.01); *Y10S 43/90* (2013.01); *Y10S 111/90* (2013.01)
USPC ............. 43/124; 43/132.1; 43/900; 111/127; 111/7.1; 111/900

(58) Field of Classification Search
USPC ............ 43/124, 132.1, 900; 47/57.5, 1.5; 11/127, 129, 7.1–7.4, 118; 239/754; 111/127, 129, 7.1–7.4, 118
See application file for complete search history.

(56) References Cited

U.S. PATENT DOCUMENTS

| 2,841,923 A | 7/1958 | Dickison |
|---|---|---|
| 3,012,526 A | 12/1961 | Baldwin et al. |
| 3,029,756 A | 4/1962 | Krivda |

(Continued)

FOREIGN PATENT DOCUMENTS

| DE | 831784 | 2/1952 |
|---|---|---|
| EP | 084486 | 7/1983 |
| WO | 0124605 A1 | 4/2001 |
| WO | 2008000970 A1 | 1/2008 |

OTHER PUBLICATIONS

International Search Report and Written Opinion for PCT/US2011/025908, dated Jun. 9, 2011.

(Continued)

*Primary Examiner* — Darren W Ark
*Assistant Examiner* — Marc Burgess
(74) *Attorney, Agent, or Firm* — Armstrong Teasdale LLP

(57) ABSTRACT

A method of treating soil adjacent a structure generally includes positioning an injection apparatus over a first injection site generally adjacent a structure. The injection apparatus is operated to inject pesticide down into the soil at the first injection site without prior disturbance of the soil at the first injection site. The injection apparatus is moved over a second injection site at least in part different from the first injection site and generally adjacent the structure. The injection apparatus is operated to inject pesticide down into the soil at the second injection site and without prior disturbance of the soil at the second injection site.

53 Claims, 15 Drawing Sheets

(56) References Cited

U.S. PATENT DOCUMENTS

| | | | |
|---|---|---|---|
| RE25,307 E | 12/1962 | Johnston | |
| 3,124,893 A * | 3/1964 | Glenn | 43/124 |
| 3,405,669 A | 10/1968 | Nimrick | |
| 3,435,785 A | 4/1969 | Harbolt | |
| 3,521,819 A | 7/1970 | Johnston | |
| 3,538,867 A | 11/1970 | Every et al. | |
| 3,550,542 A * | 12/1970 | Hollis | 43/124 |
| 3,589,054 A | 6/1971 | Pascucci | |
| 3,598,323 A | 8/1971 | Johnston et al. | |
| 3,815,525 A | 6/1974 | Kainson et al. | |
| 3,875,876 A | 4/1975 | Pustovoit et al. | |
| 4,009,666 A | 3/1977 | Russell et al. | |
| 4,624,193 A | 11/1986 | Johnston | |
| 4,637,161 A * | 1/1987 | Turner | 43/130 |
| 4,807,544 A | 2/1989 | Cross et al. | |
| 4,907,516 A * | 3/1990 | Rogers | 111/127 |
| 5,092,362 A | 3/1992 | Yie | |
| 5,101,745 A | 4/1992 | Podevels et al. | |
| 5,117,872 A | 6/1992 | Yie | |
| 5,119,744 A | 6/1992 | Comer | |
| 5,186,393 A | 2/1993 | Yie | |
| 5,207,168 A | 5/1993 | Comer | |
| 5,241,986 A | 9/1993 | Yie | |
| 5,291,842 A | 3/1994 | Sallstrom et al. | |
| 5,297,777 A | 3/1994 | Yie | |
| 5,322,418 A | 6/1994 | Comer | |
| 5,370,069 A | 12/1994 | Monroe | |
| 5,390,440 A * | 2/1995 | Mihealsick | 43/124 |
| 5,394,812 A | 3/1995 | Dunning et al. | |
| 5,487,346 A | 1/1996 | Taylor | |
| 5,503,091 A | 4/1996 | Foster et al. | |
| 5,524,821 A | 6/1996 | Yie et al. | |
| 5,575,224 A | 11/1996 | Rogers | |
| 5,605,105 A | 2/1997 | Clark et al. | |
| 5,653,292 A | 8/1997 | Ptacek et al. | |
| 5,741,090 A | 4/1998 | Dunning et al. | |
| 5,881,493 A * | 3/1999 | Restive | 43/124 |
| 5,983,559 A | 11/1999 | Manabe | |
| 6,142,084 A * | 11/2000 | Hatlø | 111/127 |
| 6,293,498 B1 * | 9/2001 | Stanko et al. | 244/134 R |
| 6,431,096 B1 | 8/2002 | Engelke et al. | |
| 6,523,298 B2 * | 2/2003 | Neumann | 43/132.1 |
| 6,722,298 B2 | 4/2004 | Engelke et al. | |
| 6,860,336 B2 | 3/2005 | Robillard | |
| 6,892,657 B2 | 5/2005 | Engelke et al. | |
| 6,939,085 B1 | 9/2005 | Posch | |
| 7,581,684 B2 | 9/2009 | Des Garennes et al. | |

OTHER PUBLICATIONS

International Search Report and Written Opinion for PCT/US2011/025919, dated Jun. 16, 2011.

* cited by examiner

METHOD OF PESTICIDE TREATMENT OF SOIL ADJACENT STRUCTURES

CROSS REFERENCE TO RELATED APPLICATION

This application claims priority to U.S. Provisional Patent Application Ser. No. 61/307,178, filed on Feb. 23, 2010, and U.S. Provisional Patent Application Ser. No. 61/307,183, filed on Feb. 23, 2010, which are incorporated herein by reference in their entirety.

BACKGROUND OF THE DISCLOSURE

The field of the disclosure relates generally to soil treatments, and more particularly to methods for applying pesticides below the ground surface using a handheld application tool that can be positioned adjacent to structures, in a manner which does not disturb the soil surface before the pesticide is injected.

The insertion of soil treatments into the soil near buildings has been used to prevent or reduce the infestation of insects or other pests. Without treatment, these pests can be become a significant nuisance or hazard to a building owner or its occupants. Such pests are known to attack the structure of buildings and may infiltrate the building causing other problems for its occupants.

At least one known method of soil treatment includes an application of pesticides, fertilizers, or other soil treatments by direct placement into the soil under and around structures, around or near ornamental plantings, poles, fences, decks, or other wooden elements. This direct placement method includes digging, trenching and/or rodding (i.e., forcing an application device into the soil), and then directly placing the soil treatment into the dug out area of the trench. This known method can cause damage to vegetation, disrupt landscaping, and greatly impact or diminish the aesthetic beauty and value of the treated area until either the plants recover or new plantings are installed.

For example, in some common termite treatments direct placement of a termiticide into the soil around structures involves the digging of a trench approximately 4 to 6 inches wide by 6 inches deep into which a termiticide composition is applied at a rate of 4 gallons per 10 linear feet of trench per foot of depth. In addition to the application of the soil treatment to the trench, soil treatment may also be dispensed into the ground through the use of a rod injection tool, which is plunged down into the ground or in the top of a footer (i.e., a part of the building's foundation). For a typical structure having a perimeter of 200 linear feet, the time to prepare, dig, inject, and finish the application of soil treatment requires at least 4 to 6 hours depending on the type of soil and whether the application is conducted by a pair of or a single technician(s).

Another known method of soil treatment includes the direct insertion of a tool down into the ground and delivering the pesticides, fertilizers, or other soil treatments into the ground Applying the soil treatments below the surface of the soil has been used as a way of limiting the wash off of the treatments. Typical devices for implementing such soil treatments have utilized needles or other mechanical devices to create a passageway into the soil to allow the soil treatment to be inserted into the ground. These devices have the obvious limitation that they create holes in the soil, which may be unsightly, or create other adverse concerns, such as unwanted soil compaction adjacent the insertion sights, as well as require the creation of the hole using mechanical forces.

The use of high pressure flows as a method of effectively injecting materials below the soil surface has been described before, such as in U.S. Pat. No. 5,370,069 to Monroe, titled Apparatus and Method for Aerating and/or Introducing Particulate Matter into a Ground Surface. These methods use high pressure jets of a fluid, such as air or water that entrain the soil treatment agent, whether the soil treatment agent is in solution with the fluid, or a granular material carried with the fluid. The high pressure jet can form a small hole in the surface into which the material is being placed, or cause the material to be absorbed by the surface in a rapid fashion, such that soil disturbance is minimal. One benefit of the use of a pressure jet is that no mechanical effort is required to create a passageway as a predicate for the soil treatment material to be placed below the surface of the soil. Nor is any other disturbance of the soil required, such as placing a tool directly down below the ground surface.

While devices such as that disclosed in Monroe are effective at placing soil treatment materials below the surface, they are designed to distribute such materials both a short distance below the soil surface and over a large open space area, where the size of the equipment is not a limitation. These known devices are not suitable for strategically injecting soil treatments into the soil under and around structures, ornamental plantings, poles, fences, decks and other wood elements where treatments relating particularly to treatments against insects infestation are common.

Accordingly, a handheld high pressure application tool for applying a termiticide or other pesticide beneath the surface of the ground adjacent a structure is needed. Such a handheld tool would permit an operator to strategically position the tool around a structure such as a house, a deck, any landscaping that may be near the house and/or deck, around utility poles, and around plants. The tool could include multiple nozzles for applying a predetermined amount of pesticide at a controlled pressure for injecting the pesticide down to a desired predetermined depth.

BRIEF DESCRIPTION OF THE DISCLOSURE

In one aspect, a method of treating soil adjacent a structure generally comprises positioning an injection apparatus over a first injection site generally adjacent a structure. The injection apparatus is operated to inject pesticide down into the soil at the first injection site without prior disturbance of the soil at the first injection site. The injection apparatus is moved over a second injection site at least in part different from the first injection site and generally adjacent the structure. The injection apparatus is operated to inject pesticide down into the soil at the second injection site and without prior disturbance of the soil at the second injection site.

In another aspect, a method of treating soil adjacent a structure generally comprises positioning a base unit of a treatment apparatus at a stationary location relative to the structure. An application tool of the treatment apparatus is positioned over a first injection site generally adjacent the structure. The application tool includes at least one nozzle. The base unit is operated to supply pressurized treatment liquid from a source of treatment liquid to the application tool. The application tool is operated to deliver pressurized treatment liquid through the at least one nozzle for injection down into the soil at the first injection site without prior disturbance of the soil at the first injection site. The application tool is moved relative to the base unit to a position over a second injection site at least in part different from the first injection site and generally adjacent the structure. The application tool is operated to deliver additional pressurized treatment liquid through the at least one nozzle for injection down into the soil at the second injection site without prior disturbance of the soil at the second injection site.

In still another aspect, a method of treating soil adjacent a structure generally comprises positioning an injection apparatus so that at least one high pressure nozzle of the injection apparatus is adjacent to the soil to be injected with pesticide. A pesticide solution is delivered to the at least one high pressure nozzle. The pesticide solution is injected into the soil by permitting the pesticide solution to flow through the at least one high pressure nozzle and into the soil without prior disturbance of the soil.

In yet another aspect, a method of treating soil adjacent a structure generally comprises positioning an injection apparatus so that at least one high pressure nozzle and at least one low pressure nozzle of the injection apparatus are adjacent to the soil. A pesticide solution is delivered to the at least one high pressure nozzle and the at least one low pressure nozzle. The pesticide solution is injected into the soil by permitting the pesticide solution to flow through the at least one high pressure nozzle and into the soil without prior disturbance of the soil. The pesticide solution is applied on the soil by permitting the pesticide solution to flow through the at least one low pressure nozzle and onto the soil.

In still yet another aspect, a method of treating soil adjacent a structure generally comprises positioning an injection apparatus so that at least one high pressure nozzle of the injection apparatus is adjacent to the soil. A pesticide solution is delivered to the at least one high pressure nozzle. The pesticide solution is injected into the soil by permitting the pesticide solution to flow through the at least one high pressure nozzle and into the soil without prior disturbance of the ground. A marking material is deposited onto the soil to indicate where the pesticide solution had been injected into the soil.

In a further aspect, a method of treating soil adjacent a structure generally comprises positioning an injection apparatus over a first injection site generally adjacent a structure. The injection apparatus is operated to inject pesticide other than vertically down into the soil at the first injection site. The operating step is performed without prior disturbance of the soil at the first injection site. The injection apparatus is moved over a second injection site at least in part different from the first injection site and generally adjacent the structure. The injection apparatus is operated to inject pesticide other than vertically down into the soil at the second injection site. The operating step is performed without prior disturbance of the soil at the second injection site.

In yet a further aspect, a method of treating soil adjacent a structure generally comprises positioning a base unit of a treatment apparatus at a stationary location relative to the structure. An application tool of the treatment apparatus is positioned over an injection site generally adjacent the structure. The application tool includes a reservoir of a treatment substance, a mixing device, and at least one nozzle. The base unit is operable to supply pressurized liquid to the application tool. The pressurized liquid is mixed with the treatment substance using the mixing device to form a pressurized treatment solution. The application tool is operated to deliver the pressurized treatment solution through the at least one nozzle for injection down into the soil at the injection site without prior disturbance of the soil at the injection site.

DETAILED DESCRIPTION OF THE DISCLOSURE

Figure 1:
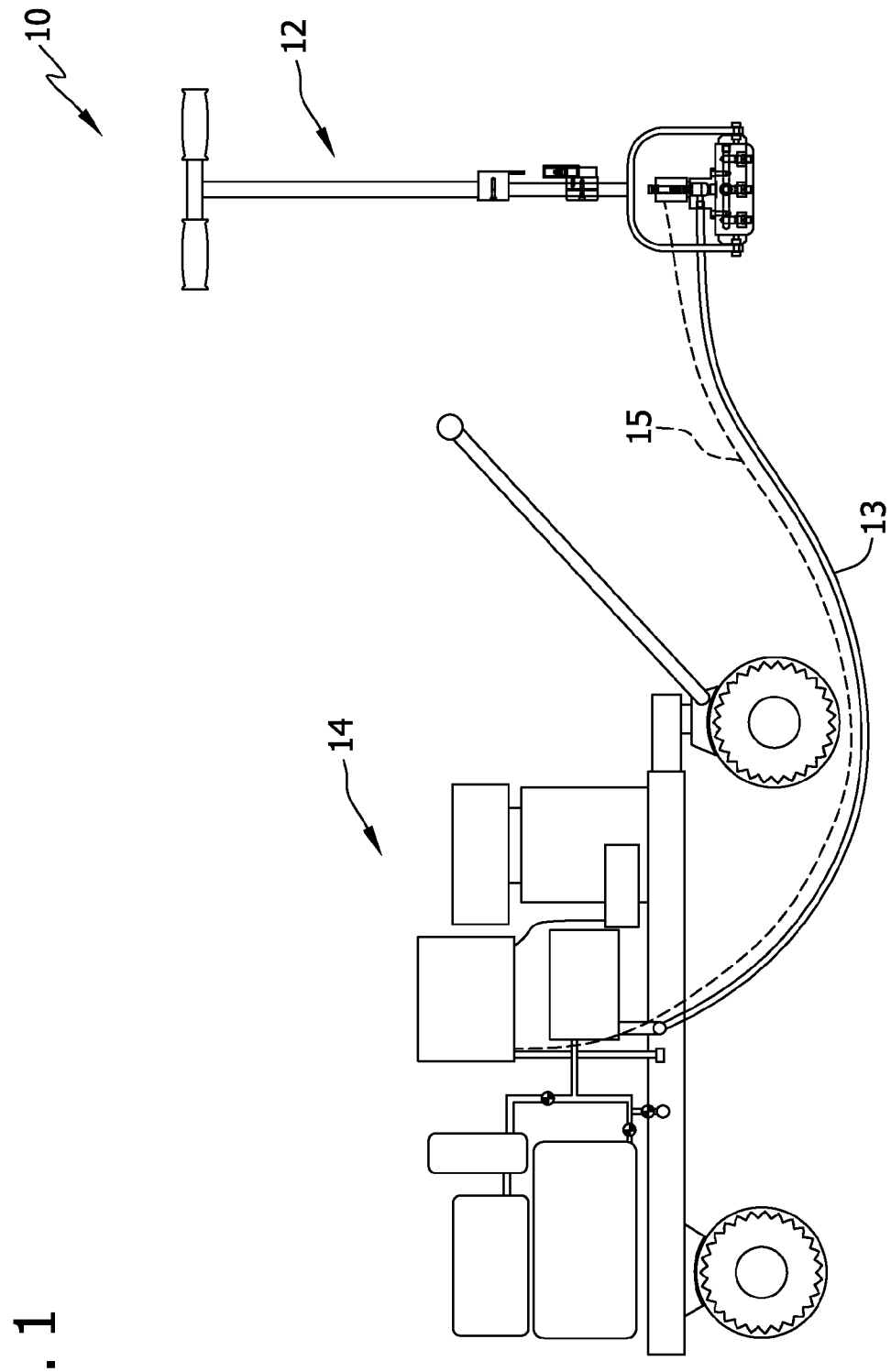
FIG. 1 is a schematic illustration of a high pressure injection system for injecting a termiticide into the ground in accordance with an exemplary embodiment in which the system includes a base unit and a handheld application tool.

A high pressure injection system for applying a pesticide, insecticide or termiticide beneath the surface of the ground is described below in detail. It is understood that the system disclosed herein can be used to apply any suitable pesticide, insecticide, or termiticide and can be used to inhibit or control various types of pests. For example, it may be desirable to inhibit and/or control termites, ants, cockroaches, beetles, earwigs, silverfish, crickets, spiders, centipedes, millipedes, scorpions, pillbugs, sowbugs, flies, mosquitoes, gnats, moths, wasps, hornets, bees, and the like. As used herein, the term "pesticide" refers to any substance or mixture for preventing, destroying, repelling, or mitigating any pest including insects, animals (e.g., mice, rats), plants (e.g., weeds), fungi, microorganisms (e.g., bacteria and viruses), pseudocoelomates (e.g., nematodes) and prions. The term "insecticide", which is a type of pesticide, is used herein to mean any substance or mixture for preventing, destroying, repelling, or mitigating insects. The term "termiticide", which is a type of insecticide, is used herein to mean any substance or mixture for preventing, destroying, repelling, or mitigating termites.

Although the methods and systems described herein relate to the application of termiticides beneath the surface of the ground, the methods and systems could also be used to apply pesticides, insecticides, or other soil treatments. The use of termiticides as described herein is not intended to be limiting in any way. Rather, it is for exemplary purposes. The methods and systems described herein may be used, therefore, to apply any type of soil treatment beneath the ground (e.g., pesticides, fertilizers, other soil conditioning materials and insect treatments including insecticides placed around the perimeter of a structure), and is in no way limited to only termiticides.

The methods and systems described herein include a termiticide fluid supply cart (a base unit), and a portable handheld application tool that facilitates the application or injection of termiticides into the soil under and around structures, ornamental plantings, poles, fences, decks and other wood elements. The example embodiment eliminates the need to apply termiticides using certain known techniques such as digging, trenching, and/or rodding, which all require mechanically disturbing at least the surface of the ground or soil. These known techniques can cause damage to vegetation, disrupt landscaping, and impact or diminish the aesthetic beauty and value of the treated area until the plants recover or new plantings are installed.

The application system described herein includes an application tool that has a tee-handle at the top of the tool and a manifold assembly at the bottom of the tool. The tee-handle includes a hand grip portion on each side of a vertical shaft that extends between the handle and the manifold assembly. The hand grip portions may include rubber grips to aid in holding the tool during application and to reduce hand strain. The vertical shaft of the tool consists of several parts that allow the shaft to compress, when the handle is pushed down, much like a pogo stick. The compression of the shaft activates an electronic triggering switch (broadly, "an actuator") that temporarily opens a discharge valve, for example a poppet. When the operator has the manifold assembly (i.e., device plate) in position on the ground, the operator uses the handle to apply a downward pressure (approximately 15-20 pounds) onto the shaft to actuate the trigger switch, which in turn causes a single injection of termiticide into the ground. The operator must release the pressure applied to the shaft to disengage the switch, which results in the system being reset.

In the example embodiment, the switch actuates the discharge valve a single time for each compression of the shaft. Thus, for each compression of the shaft, the discharge valve is opened a single time and a predetermined quantity of termiticide is discharged from the tool. The switch of tool is reset when the shaft is released. The next application can then be made by again compressing the shaft.

The application tool also includes a mounting bracket that mounts the manifold assembly to the shaft. This bracket allows the application head or manifold assembly to pivot about at least one axis. This allows the operator to adjust the tool such that the manifold assembly is properly positioned before activating the application switch.

The manifold assembly includes an inlet port, a discharge valve, a plurality of high pressure nozzles, a manifold head, and a contact plate for protecting the plurality of high pressure nozzles. The system also includes at least one high pressure liquid line and electrical connections that extend between the supply cart and the handheld application tool. The system also includes a pressure manifold and an electronic controller (broadly, "a valve closer") that sets the length of time the discharge valve remains open during each activation of the electronic switch.

In operation, a measured dose of a liquid termiticide concentrate from a container housed on the supply cart is mixed with measured supply of water and fed to the application tool by an inline injection system. In another embodiment, the termiticide solution is supplied to the application tool from a tank or container without the need of an inline injection pump or device. In yet another embodiment, the termiticide concentrate can be carried by the operator and housed in a transportable container formed into and/or held within a backpack, a shoulder holster or sling, a belt holster, a leg holster, or other suitable device capable of holding the pesticide container.

The methods and systems described herein utilize high pressure to inject the termiticide into soil beneath the surface of the ground. The high pressure injection system described herein differs from at least some known liquid injection systems that apply termiticides for soil application in that the current industry standard liquid termiticide injection systems inject liquids into the ground using pressures of 25 to 35 psi and through a single injection port or tip. The example system described herein injects the termiticide solution into the ground at pressures ranging from about 50 psi to about 10,000 psi, and in another embodiment, from about 1,000 psi to about 7,000 psi, and in yet another embodiment, at about 4,000 psi.

In operation, the application tool is set at a desired pressure for applying the termiticide. The operator then places the manifold assembly, and more specifically, the contact plate, which protects the injection nozzles, in a desired application area. The desired area may be adjacent to a wall or foundation of a structure. The operator then press down on the application handles to compress the shaft of the tool. This downward pressure causes the upper and lower portions of the device shaft to come together thereby activating an electronic switch. The switch would temporarily open the discharge valve and allow a predetermined amount of termiticide solution to pass through the high pressure injection nozzles and into the ground. The switch would only allow a single charge (i.e., a predefined amount of termiticide solution) to pass through the nozzles. The switch is reset by releasing the pressure on the handle and allowing the two parts of the electronic switch to separate. The operator applicator would then lift or slide the handheld application tool along the wall to the next application point and press down on the handle again, thus repeating the injection of the termiticide solution into the soil. The operator continues to move the handheld application tool and inject termiticide until the desired application is area is injection. In one example, the desired application area is the perimeter of the structure so that a barrier of termiticide completely surrounds the structure and thereby inhibits termites from passing through the barrier to the structure.

In an alternative embodiment, the electronic switch could be positioned on or near the tee-handle portion of the tool where it could be activated by the operator pressing down on a button or switch with a finger or thumb. In another embodiment, the tool could include a position marker, such as a foam, dust, powder, paint, or a dye material that would be applied when the termiticide is applied. The position marker would apply a marking material to the ground to mark the position of the contact plate during each application. This would allow the operator to visually determine where an application has been made and where the device plate should be re-positioned to ensure that a continuous application of the termiticide is made around the perimeter of the structure. The marker would also aid in preventing over or under application of the termiticide solution in the application area.

The high-pressure application tool and methods of using the same as described herein have many advantages over the known systems. For example, the tool described herein may include an inline injection assembly which eliminates the need to mix large volumes of the termiticide solution, and reduces the hazards associated with transporting or handling large volumes of termiticide solutions on public roadways or on private property. The use of the high-pressure injection tool also eliminates the need for digging (i.e., trenching) before applying the termiticide solution into the ground. This reduces the destruction of the landscaping and/or natural vegetation around the perimeter of a structure being treated. The high-pressure injection tool also reduces or eliminates the need for rodding into the soil with an application device in order to apply the termiticide solution. The high-pressure tool can also be programmed to deliver a specific volume of termiticide solution per nozzle, and control the depth to which the solution penetrates into the soil by controlling the application pressure. By controlling the volume and the pressure, the application volume of the termiticide can be reduced by 25% to 80% of a normal liquid termiticide application, thus saving cost and reducing demands on water. This is especially important in drier climates or during times of drought. The high-pressure tool also greatly reduces the time required to complete a termiticide treatment around a structure. This reduction in time can range between 40% and 80%. As a result, less time is spent at the site and thereby labor costs associated with the site preparation and application are reduced. Also, the application tool, which is designed to place the injection nozzles in close proximity to the ground when injecting the termiticide into the ground, reduces the risk of exposure to the operator or anyone in the immediate area of the application.

Referring to the drawings, FIG. 1 is a schematic illustration of a high pressure injection system 10 for injecting termiticide into the ground in accordance with an exemplary embodiment of the present invention. The injection system 10 includes a handheld portable application tool 12 (broadly, an "injection apparatus") and a termiticide fluid supply cart 14 (broadly, a "base unit"). The application tool 12 is connected to the cart 14 via a conduit 13 defining a fluid passageway (e.g., a hose) and at least one electrical connection 15. The conduit 13 permits fluid (e.g., water and/or a termiticide solution) to flow from the cart 14 to the application tool 12. The electrical connection 15 is used for transmitting various control signals between the application tool 12 and the cart 14.

Figure 2:
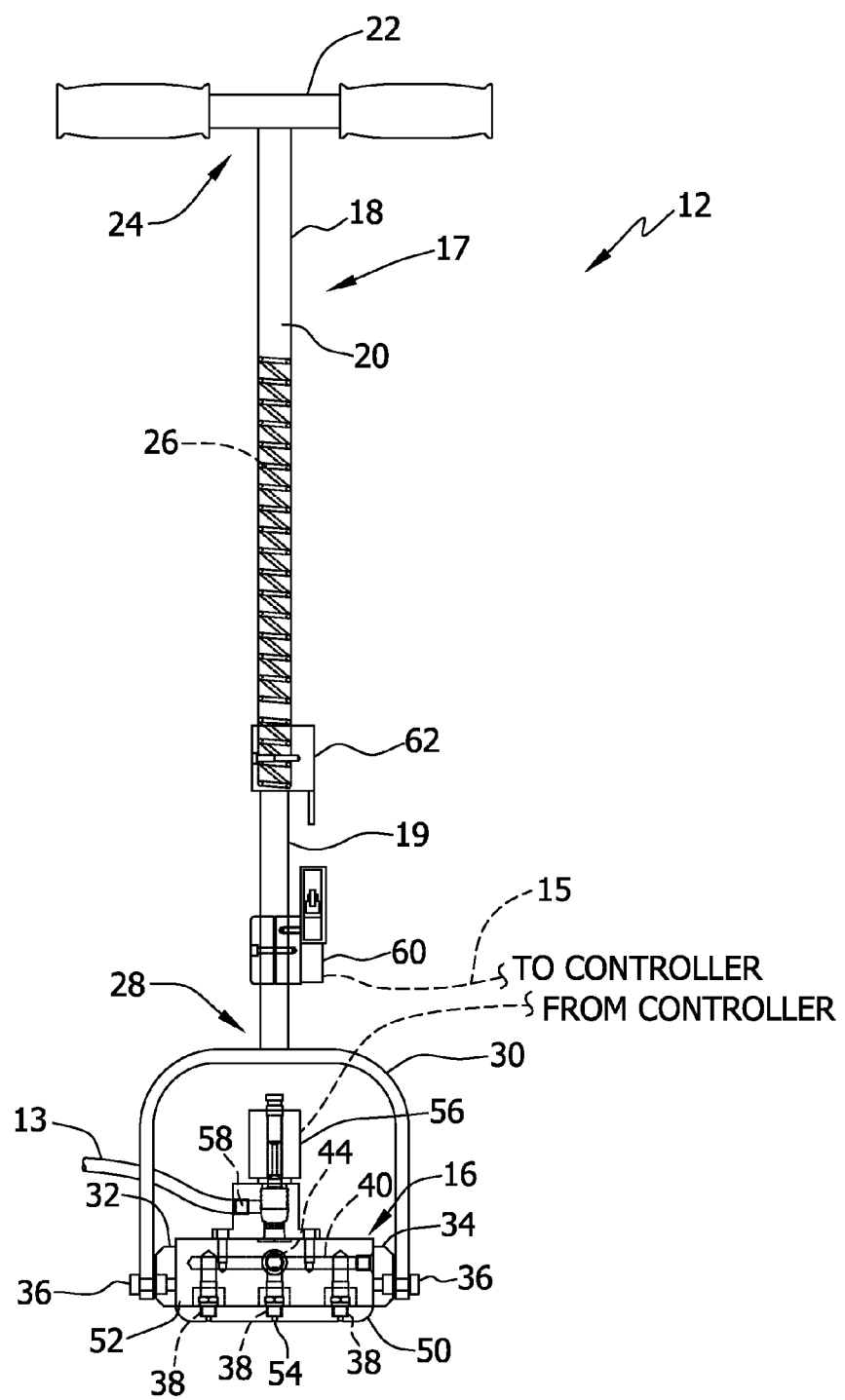
FIG. 2 is a front view schematic illustration of the handheld portable application tool of FIG. 1 with parts cut away.
Figure 3:
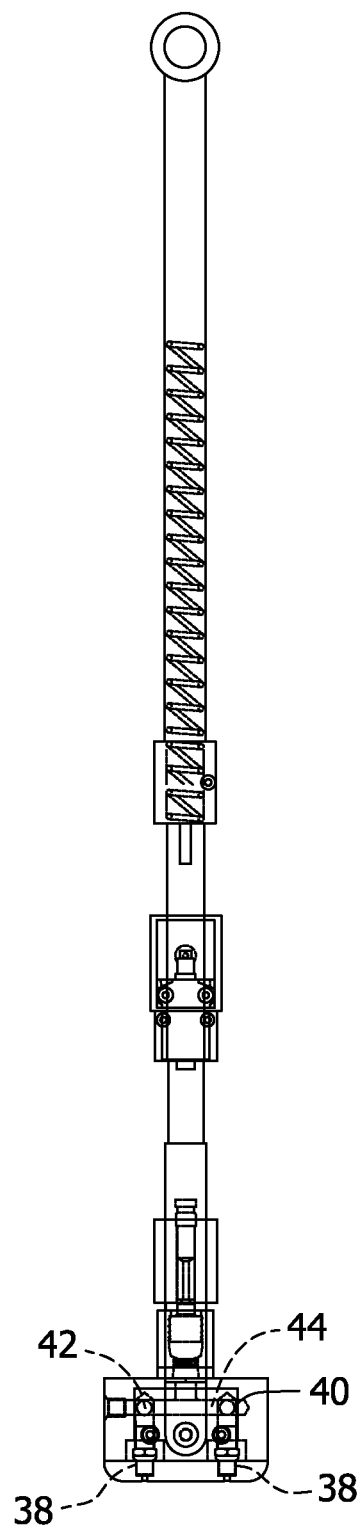
FIG. 3 is a side view schematic illustration of the handheld portable application tool of FIG. 2.

FIG. 2 is a front view schematic illustration of the handheld portable application tool 12, and FIG. 3 is a side view schematic illustration of the application tool 12. The handheld portable application tool 12 includes a handle 17 and a manifold head 16 mounted to the handle. The handle 17 includes an upper portion 18 and a lower portion 19. The upper portion 18 includes a tubular section 20 and a hand grip section 22 attached to an upper end 24 of the tubular section 20. As a result, the upper portion 18 of the handle 17 has a generally T-shape. The lower portion 19 of the handle 17, which is tubular, is sized for insertion into the tubular section 20 of the upper portion 18 of the handle. With the lower portion 19 of the handle 17 inserted into the tubular section 20 of the upper portion 18 of the handle, the upper portion can move with respect to the lower portion from a first, extended position to a second, compressed position. A biasing element, such as a spring 26, is provided to bias the upper portion 18 of the handle 17 toward its first, extended position. It is understood, however, that any known biasing element 26 may be used. A flange (not shown) or other suitable retainer(s) may be provided to inhibit the lower portion 19 of the handle 17 from being pulled or otherwise withdrawn from the upper portion 18 to thereby ensure that the lower portion remains telescopically attached to the upper portion. A lower end 28 of lower portion 19 of the handle 17 is attached to an inverted U-shaped attachment bracket 30. The manifold head 16 is pivotally attached at each of its ends 32, 34 to the attachment bracket 30 via a pair of pivot pins 36.

The manifold head 16 includes at least one internal passage to distribute the termiticide to a plurality of high pressure nozzles 38 in fluid communication with the internal passage. As seen in FIG. 3, the illustrated manifold head 16 includes two main internal passages 40, 42, and a cross passage 44 connecting main internal passages. It is contemplated that the manifold head 16 may include any number of high pressure nozzles 38. For example, the manifold head 16 of the exemplary embodiment has a matrix of six high pressure nozzles 38 with each nozzle generally equidistant from each other. Each of the high pressure nozzles 38, in one embodiment, has an orifice diameter ranging from about 0.002 inch to about 0.01 inch.

With reference again to FIG. 2, a contact plate 50 is attached to a bottom surface 52 of the manifold head 16 to protect the high pressure nozzles 38. In the illustrated embodiment, the contact plate 50 includes a plurality of openings 54 with each of the openings being generally aligned with a respective one of the plurality of high pressure nozzles 38. As a result, the high pressure nozzles 38 are spaced from the soil by the contact plate 50 and therefore do not directly contact the soil. Moreover, the contact plate 50 shields or otherwise blocks soil, rocks, and/or other debris that may be "kicked-up" during the injection of the termiticide. The contact plate 50 includes rounded edges to facilitate sliding of the tool 12. The contact plate 50 can be made from any suitable material, for example, metal and/or plastic.

Figure 4:
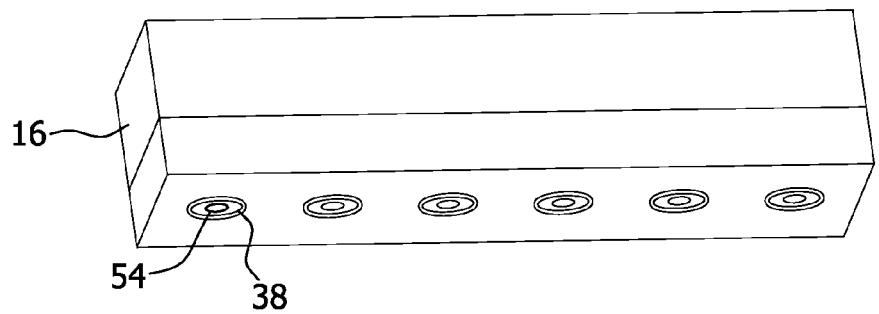
FIG. 4 is a perspective schematic illustration of an elongated shaped manifold head for use with the application tool.
Figure 5:
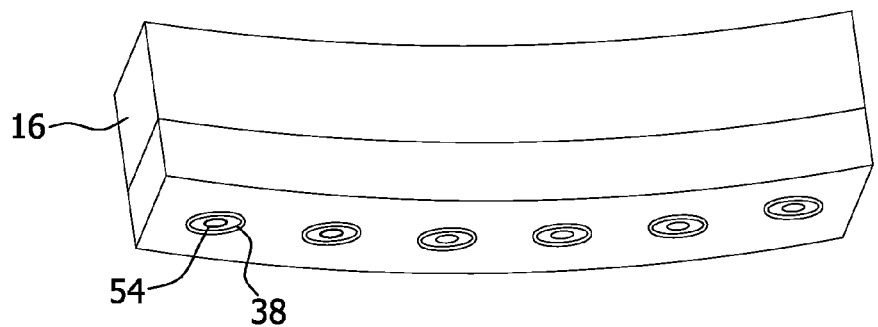
FIG. 5 is a perspective schematic illustration of an arcuate shaped manifold head for use with the application tool.

The size and shape of the manifold head 16 may be selected based on the particular application for which the tool 12 is intended to be used. In one embodiment, the manifold head 16 has a shape with a high length to width ratio such as the high pressure nozzles 38 being arranged linearly in a row as shown in FIG. 4. In another embodiment, the manifold head 16 has an arcuate shape as shown in FIG. 5. The arcuate shaped manifold head 16 may be used to conform around circular edges, such as around trees. It is contemplate that the manifold heads 16 can be interchangeable. That is, the operator of the tool 12 can selectively change out the manifold head 16. It is also contemplates that the manifold head 16 can be replaced with other delivery means (e.g., a rod injection tool) for delivering a supply of termiticide at low pressures. These low pressure delivery means can be used in areas less suitable for high pressure injection.

The weight of the manifold head 16 may be selected so that the mass of the manifold head 16 assists in retaining tool 12 in position during a discharge from the plurality of high pressure nozzles 38, without being unduly burdensome for manual positioning and moving the tool by an operator. In general, the lighter the mass of the manifold head 16, the greater the force that the operator must apply to the handle 17 to retain the tool 12 in position during a discharge of termiticide from the high pressure nozzles 38.

As illustrated in FIG. 2, a discharge valve 56 is attached to the manifold head 16 and is in fluid communication with the internal passages 40, 42, 44 in the manifold head and the supply of termiticide. More specifically, one end of the discharge valve 56 is coupled to a high pressure inlet port 58 and the other end of the discharge valve is coupled to the hose 13. The discharge valve 56 is moveable between an opened position and a closed position. When the discharge valve is in its closed position, termiticide is inhibited from flowing from the supply of termiticide via the hose 13 to the internal passages 40, 42, 44 in the manifold head via the high pressure inlet port 58. When the discharge valve 56 is opened, the termiticide solution flows from the supply of termiticide through the hose 13 and into inlet port 58 under high pressure. From the inlet port 58, the pressurized termiticide flows into internal passages 40, 42, 44 of the manifold head 16 and through the high pressure nozzles 38 from which the termiticide is injected into the ground. In one embodiment, the termiticide is pressurized to a pressure of about 25 psi to about 10,000 psi, and in another embodiment, from about 1,000 psi to about 7,000 psi, and in yet another embodiment, at about 4,000 psi.

In one suitable embodiment, the discharge valve 56 is a solenoid operated poppet valve capable of sufficiently rapid operation to allow opening and closing of the discharge valve 56 within the desired time parameters to allow correct depth penetration of the soil based on the pressure in use and correct volume of termiticide solution for the specific application. While it is possible to use a hydraulically actuated valve, the size and weight constraints of such a valve may otherwise limit the utility of the handheld application tool 12.

In another suitable embodiment, the manifold head 16 may have a discharge valve 56 associated with each of the high pressure nozzles 38, such that even distribution of termiticide fluid across the plurality of high pressure nozzles 38 may be ensured. While discharge balancing can be obtained within reasonable parameters simply through proper sizing of the internal passages 40, 42, 44, should it be required, and should it justify the expense, multiple discharge valves 56 may be used, such that pressurized termiticide solution contained in a feed hose supplying each of the discharge valves 56 may provide that an adequate amount of termiticide solution is available for each of the high pressure nozzle 38. Such a configuration, however, adds complexity to the system 10 in that the controller must be able to actuate the multiple discharge valves 56 in response to a single actuation, i.e., increasing the amount of wiring and power required to control the valves, although the power requirement may be offset by the use of smaller discharge valves 56.

As illustrated in FIG. 2, a trigger switch 60 (broadly, an "actuator") is mounted on the lower portion 19 of the handle 17 and a trigger switch actuator 62 is mounted on the upper portion 18. The trigger switch 60, which is electrically coupled to the discharge valve 56, activates the discharge valve 56 when the trigger switch actuator 62 engages the trigger switch 60. In the illustrated embodiment and as seen in FIG. 3, the trigger switch actuator 62 is engaged with trigger switch when the upper portion 18 of the handle 17 is moved to its second, compressed position. Thus, the trigger switch 60 can be actuated by moving the upper portion 18 of the handle 17 from its first, expanded position to its second compressed position by applying a force on the upper portion so that it slides downward relative to the lower portion 19 of the handle until the trigger switch actuator engages the trigger switch 60.

In another embodiment (not shown), the trigger switch 60 can be located on the hand grip section 22 of the upper portion 18 of the handle 17 where it can be actuated by the operator using a finger or thumb. The trigger switch may be a mechanical device, which interrupts the flow of termiticide from the discharge valve 56 to the high pressure nozzles 38, or may be an electrical switch which interrupts the electrical signal to the discharge valve 56, thus preventing actuation of the discharge valve 56.

To inject the termiticide into the ground, the operator positions handheld portable application tool 12 such that the contact plate 50 is in contact with the surface of the ground. A downward force between about 15 to 20 pounds is applied by the operator to the upper portion 18 of the handle 17 to move the upper portion 18 from its first position to its second position and thereby cause the trigger switch actuator 62, which is mounted to the upper portion, to engage the trigger switch 60, which is mounted to the lower portion 19. Engagement of the trigger switch actuator 62 and the trigger switch 60 actuates the trigger switch 60. As a result, an electronic signal is sent from the trigger switch 60 to the discharge valve 56 causing the discharge valve to move from its closed position to its opened position for a predetermined amount of time thereby permitting termiticide to flow to and out the high pressure nozzles 38 for injecting the termiticide into the ground. The operator then releases the pressure from the handle 17, which resets the trigger switch. More specifically, the spring 26 causes the upper portion 18 of the handle 17 to move back to its first, extended position. The illustrated trigger switch 60 is configured to work only once during each compression of handle 17 to prevent repeated opening of the discharge valve 56 until the handle 17 has been reset.

The depth of penetration of the termiticide solution into the ground is a function of the pressure at which the termiticide solution is discharged from the tool 12 and the type of soil into which the termiticide is discharged. For example, hard packed or compacted soil, such as clay, is harder to penetrate and may require higher pressures than a soft sandy soil. Thus, at a given pressure the penetration of termiticide into a sandy soil may be about 12 to 14 inches, while the penetration of termiticide into a sandy loam at the same pressure may be about 6 to 9 inches, and the penetration of termiticide into a clay soil at the same pressure may be about 2 to 5 inches.

Referring to FIG. 5, the manifold head can be formed into an arch, a semicircle, or other form of angled deflection. A manifold formed in such a manner would be well suited for facilitating the injection of a pesticide solution around a tree, a bush, a pole, a potted plant, root ball, or other plant or structural element where the curved or angled manifold enables the applicator to position the pesticide into an area proximate to the targeted point of application.

Figure 6:
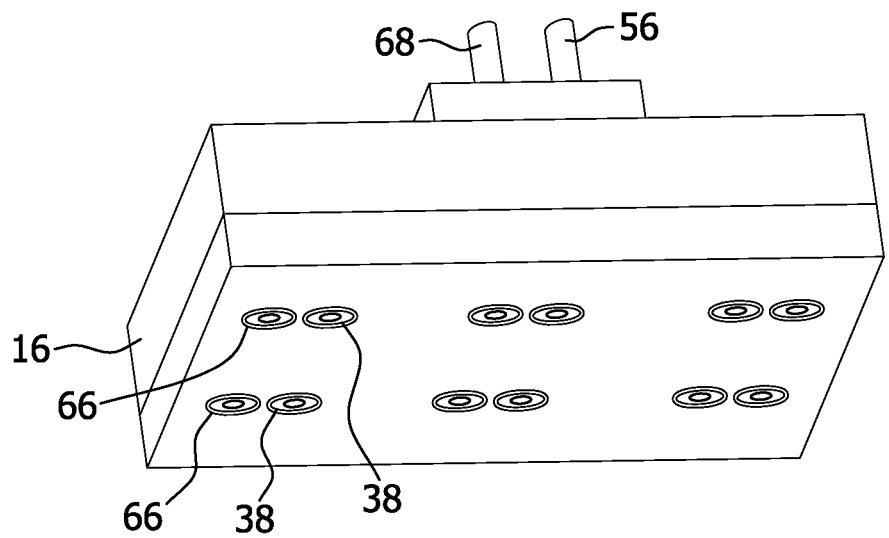
FIG. 6 is a perspective schematic illustration of the manifold head shown in FIG. 2 having low pressure nozzles positioned adjacent to high pressure nozzles.
Figure 7:
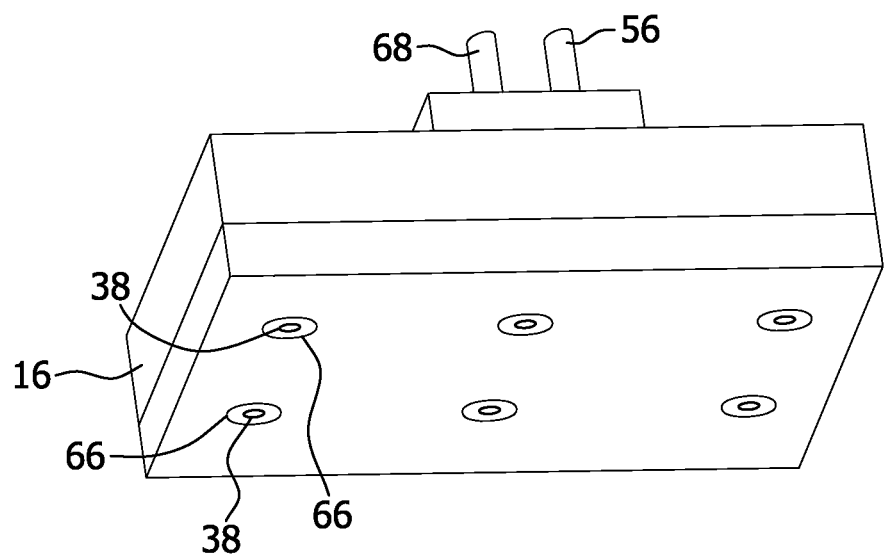
FIG. 7 is a perspective schematic illustration of the manifold head shown in FIG. 2 having low pressure nozzles concentric with high pressure nozzles.

Referring also to FIGS. 6 and 7, the manifold head 16 may also include a plurality of the low pressure nozzles 66. In the illustrated embodiment of FIG. 6, each of the lower pressures nozzles 66 positioned adjacent to one of the plurality of high pressure nozzles 38. In another embodiment, which is illustrated in FIG. 7, each of the low pressure nozzles 66 is concentric with one of the high pressure nozzles 38. The low pressure nozzles 66 apply the termiticide solution onto the surface of the ground when a low pressure discharge valve 68 is opened. The lower pressure discharge valve operates in the same manner as the previously described discharge valve 65. The low pressure nozzles 66 are configured to apply the termiticide solution to the ground at a pressure of less than about 35 psi.

Figure 8:
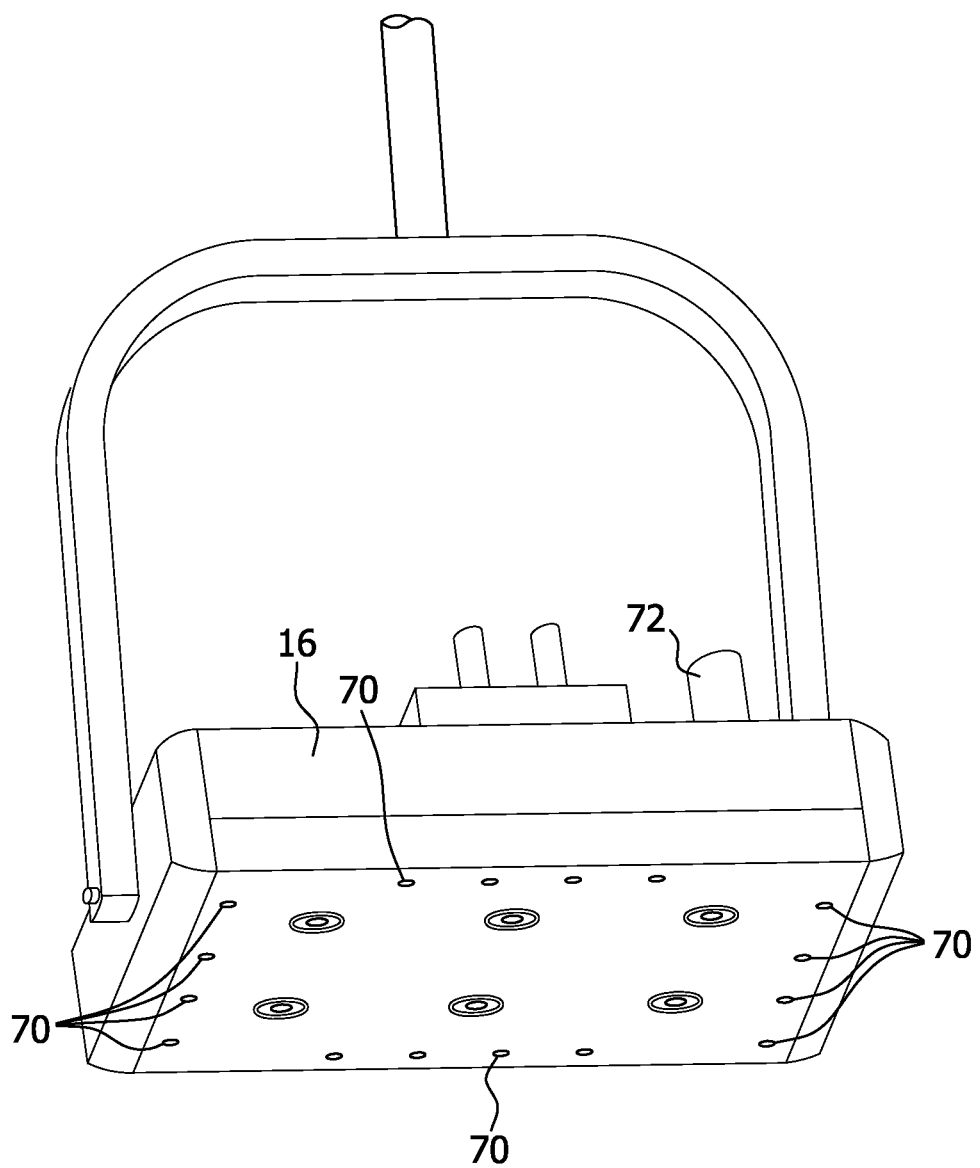
FIG. 8 is a bottom schematic illustration of the manifold head shown in FIG. 2 having nozzles on the perimeter for applying marking materials.
Figure 9:
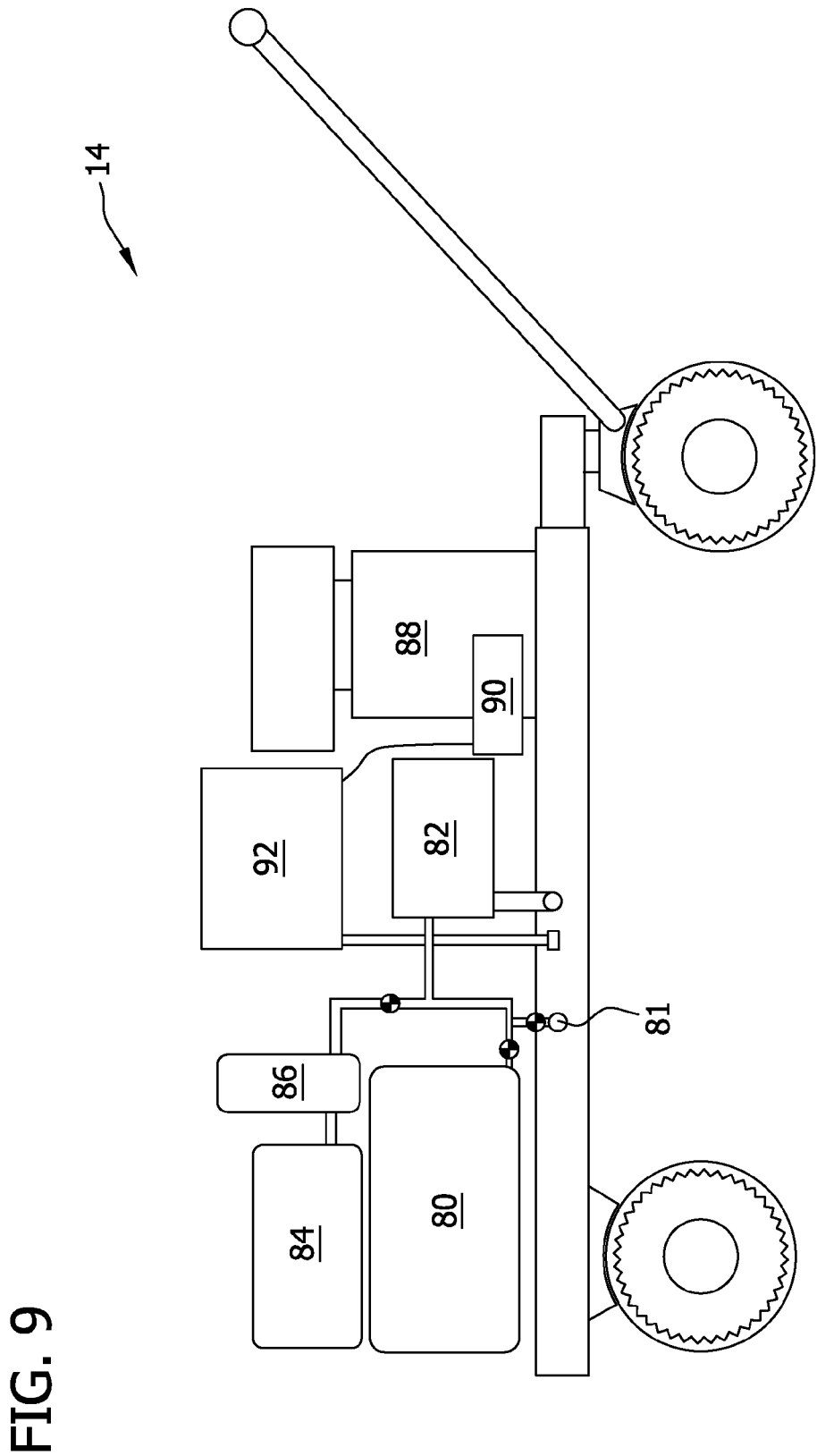
FIG. 9 is a side view schematic illustration of the base unit shown in FIG. 1.

Referring now to FIG. 8, the handheld portable application tool 12 may also include a plurality of nozzles 70 (broadly, a "dispenser") for depositing position marker material onto the surface of the soil to indicate an area in which the termiticide has been injected, and marking the position of the manifold head 16 during each application. Marking the position of the manifold head 16 permits the operator to visually observe where termiticide has been applied and to where the manifold head should be positioned next so that a uniform application of the termiticide can be applied around the perimeter of a structure. In addition, the applied marking material may also aid in preventing over and/or under application of the termiticide. Any suitable marking material may be used, for example, a foam, a powder, a paint, and a dye. In the illustrated embodiment, the marking material is applied by the plurality of nozzles 70 about the circumference of the manifold head 16. A container 72 containing the marking material may be carried by the application tool 12 or a remotely located device such as the cart 14 shown in FIG. 1. It is understood that the marking material may be applied by any suitable delivery device and remain within the scope of this invention.

The supply of termiticide solution may be provided by the supply cart 14. In one embodiment, the cart 14 includes a water reservoir 80, a high pressure pump 82 for pressurizing the termiticide solution, a termiticide concentrate reservoir 84, and a mixing device 86 that supplies the appropriate amount of termiticide concentrate to be mixed with the appropriate amount of water to form the termiticide solution. A water inlet 81 for receiving water from an external water source (e.g., a standard residential water spigot) is also provided. It is contemplated that either the water reservoir 80 or the water inlet 81 can be omitted. The supply cart 14 also includes a gasoline engine 88 with a generator 90 for generating power for operating the pressure pump 82 and generating electrical current for operating a controller 92 associated with the tool 12. In another embodiment, electrical power can be supplied by connecting into an electrical outlet located at the application site.

It is contemplated that the supply cart 14 may be vehicle mounted (e.g., a truck, a van, a ATV), trailer mounted, self propelled, or even a combination thereof, such that the cart 14 can be towed to a job site, then moved around a location under its own power. It is also contemplated that some the various components of the system 10 described herein as being mounted on the supply cart 14 may be mounted on the application tool 12. For example, it is contemplated that the termiticide concentration reservoir 84 and the mixing device 86 can be mounted on the application tool 12 instead of the supply cart 14. It is further contemplated that the supply cart 14 can be omitted. In such an embodiment, at least the termiticide concentration reservoir 84, the mixing device 86, and the water inlet 81 are carried on-board the application tool 12.

The controller 92, which is mounted on the cart 14, permits the operator of the system 10 to selectively set a pulse duration and pressure level for termiticide injections. The controller 92 may be programmable to permit the operator to enter parameters associated with a particular manifold head 16 in use, such as by defining the number of orifices and their sizes, parameters with a termiticide solution in use, such that dosing through the mixing device 86 can be properly controlled, or the number of injections can be tracked, and the like.

Figure 10:
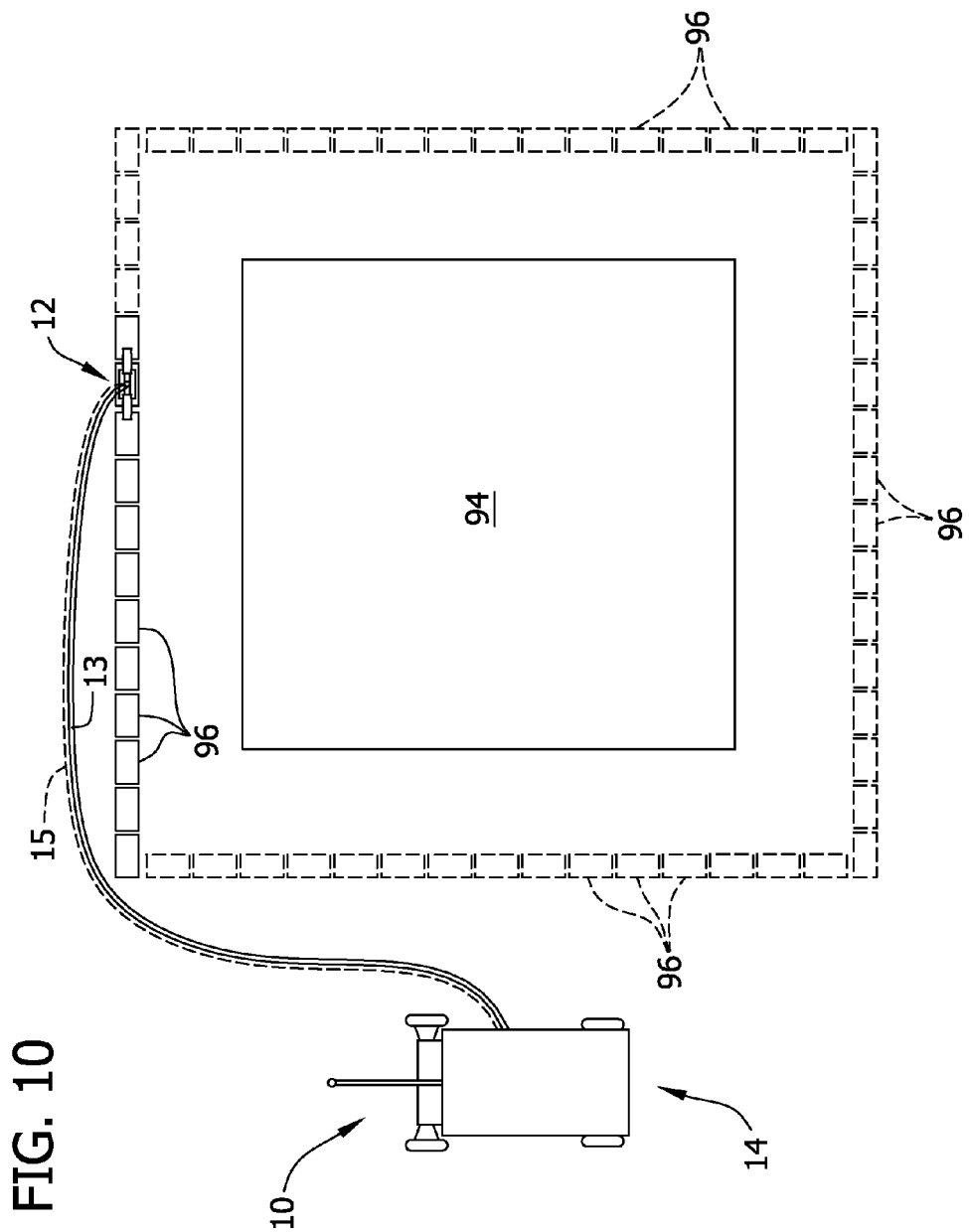
FIG. 10 is a top plan schematic illustrating the high pressure injection system of FIG. 1 being used to inject termiticide into the soil adjacent a structure.

As illustrated in FIG. 10, the system 10 can be used according to one embodiment of a method for treating soil adjacent to a structure, such as a house 94. For example, the system 10 can be used to inject and/or apply termiticide to the soil around the perimeter of the house 94 and thereby establish a barrier to inhibit termites from accessing the house and to control termites in close proximity to the house. According to one method, the base unit 14 is placed at a stationary location relative to the house 94 and the tool 12 is positioned over, and more suitably in contact with, an injection site 96 generally adjacent the house. The tool 12 is operated as described above to inject termiticide down into the soil at the injection site 96 without prior disturbance of the soil. The tool 12 is then moved relative to the supply cart 14 to another injection site 96 that at least in part different from the previous injection site and generally adjacent the house 94. In the illustrated embodiment, the injections sites 96 are generally in side-by-side relationship with each other. The tool 12 is again operated to inject termiticide down into the soil at this next injection site 96 without prior disturbance of the soil.

As seen in FIG. 10, the tool 12 is moved to and operated at a plurality of injection sites 96 adjacent the structure so that the injection sites cooperatively surround substantially the entire perimeter of the house 94. FIG. 10 illustrates a plurality of injection sites 96 at which termiticide has been injected (illustrated in the Figure with solid lines) and a plurality of injection sites at which termiticide will be injected (illustrated in the Figure with dashed lines). It is understood that termiticide can also be applied to surface of the soil at each or some of the injection sites 96. It is further understood that marking material can be deposited onto the soil to indicate where the pesticide solution had been injected into the soil. It is also contemplated that, if necessary, the supply cart 14 may be moved to another location as the handheld tool 12 is used about the perimeter of the house 94.

Figure 11:
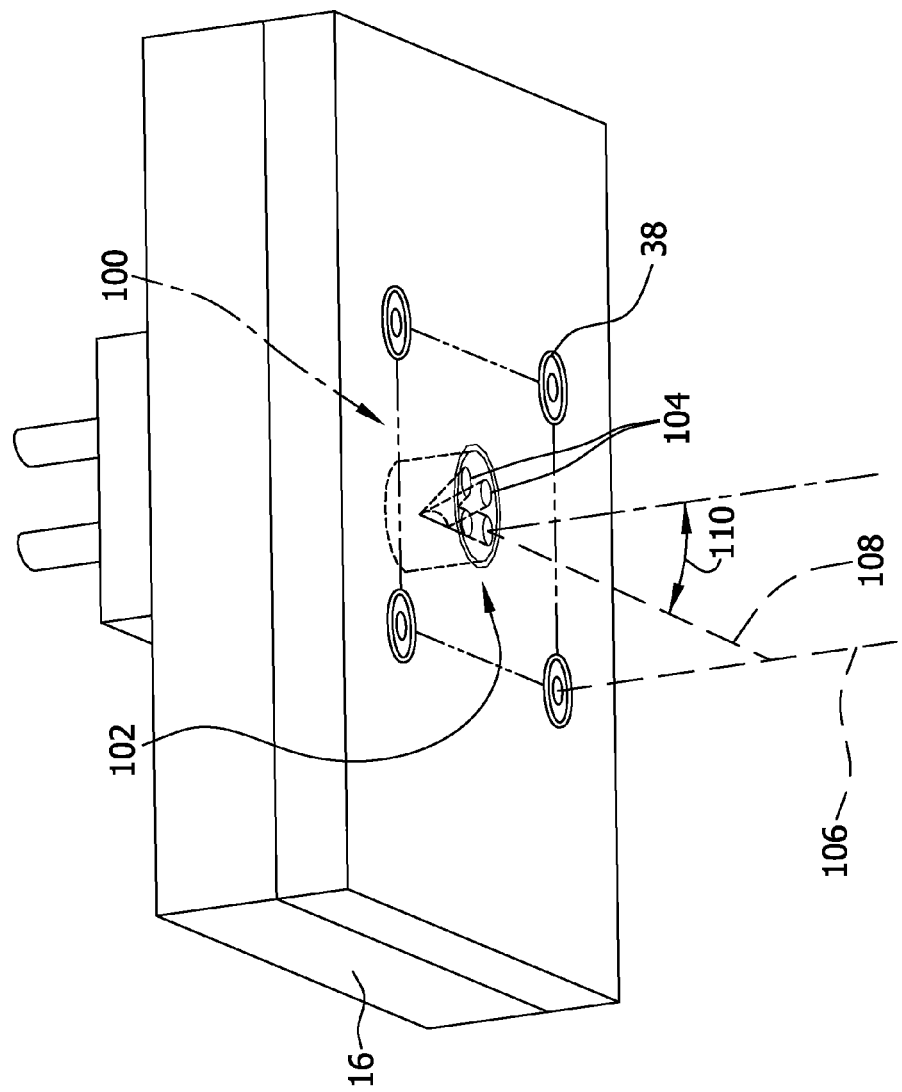
FIG. 11 is a perspective schematic illustration of a manifold head that includes multiport center nozzles.
Figure 12:
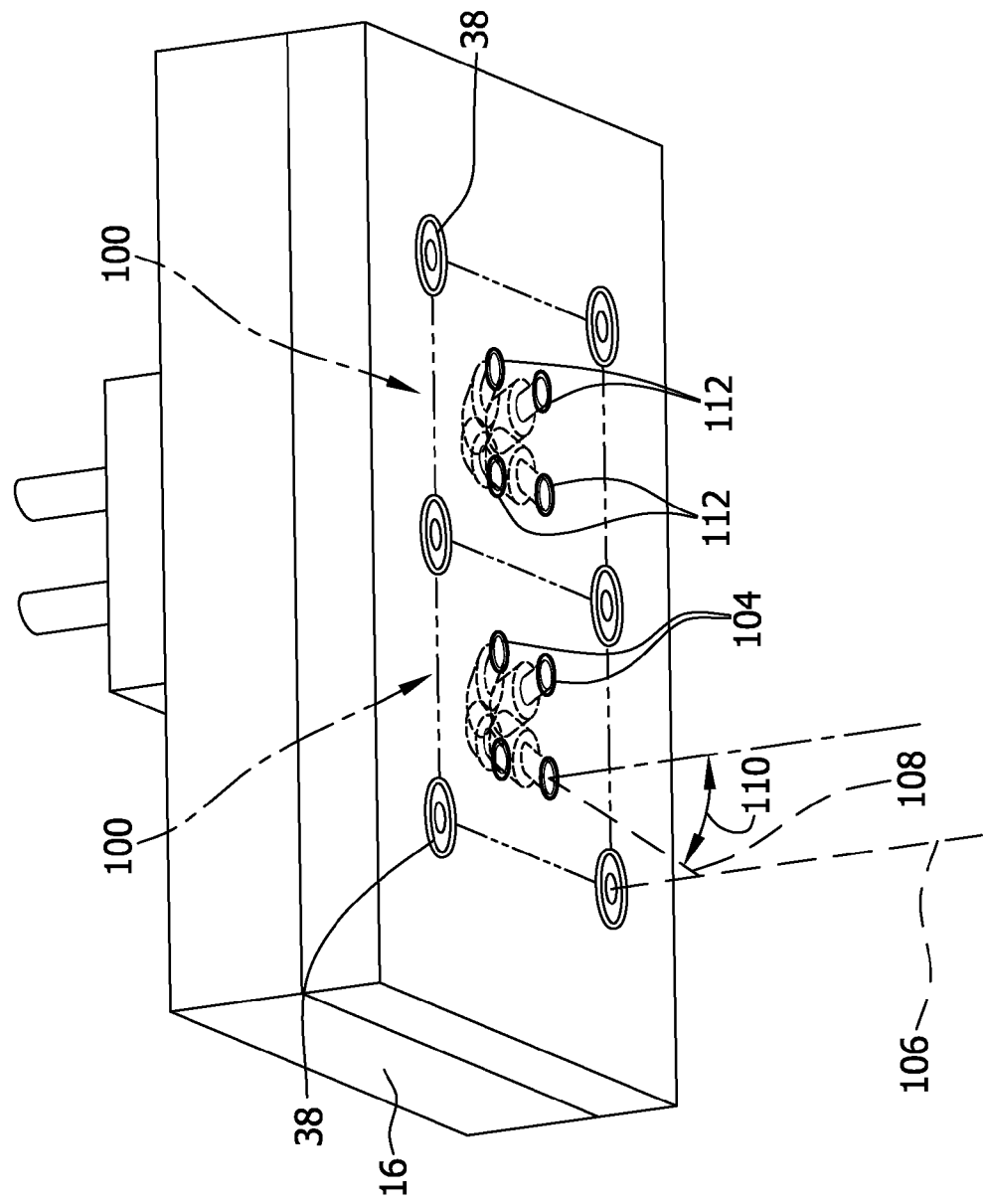
FIG. 12 is a perspective schematic illustration of a manifold head that includes four center nozzles.

Referring now to FIG. 11, in another embodiment the manifold head 16 includes four high pressure nozzles 38 arranged in a rectangular and more suitably a square matrix configuration 100 wherein adjacent nozzles 38 are generally equidistant from each other. In the illustrated embodiment, each of the high pressure nozzles is generally positioned at each corner of the square matrix configuration 100. It is contemplated that more than one square matrix of high pressure nozzles 38 may be formed in the manifold head 16. For example, FIG. 12 illustrates an embodiment wherein six high pressure nozzles 38 form two side-by-side square matrices 100 (or a single rectangular matrix). It is contemplated that the manifold head 16 may include 4+x equidistant high pressure nozzles 38 forming 1+(x/2) side-by-side square matrices 100, wherein x is an even integer greater than 0. It is also contemplated that the high pressure nozzles 38 can be arranged in an orthogonal matrix configuration, for example, a rectangular matrix, an hexagonal matrix, an octagonal matrix, and the like.

As seen in FIGS. 11 and 12, a multiport high pressure nozzle 102 can be positioned in the center of each of the square matrices 100. Each of the illustrated multiport nozzles 102 includes four ports 104 that are angled toward the corners of matrix 100. Each of the high pressure nozzles 38 is orientated so that a discharge stream 106 of termiticide from the nozzle 38 is substantially perpendicular to the bottom surface 52 of the manifold head 16. When the manifold head 16 is positioned on the ground, the discharge stream 106 is substantially normal to the ground surface, e.g., vertical, when the surface of the ground is substantially level. Each of the ports 104 of the multiport nozzle 102 is configured to direct a discharge stream 108 of termiticide from the port to intersect the discharge stream 106 from one of the high pressure nozzles 38. The intersection of the discharge stream 106 from one of the high pressure nozzles 38 by the discharge stream 108 from one of the ports 104 of the multiport high pressure nozzle 102 may be about 1 inch to about 12 inches below the surface of the ground. An angle off vertical 110 of the discharge stream 108 of one of the ports 104 of the multiport nozzle 102 is based on the depth of intersection desired and the distance between the nozzles 38. The intersection of the discharge streams potentially results in the pooling of some of the injected termiticide. For example, when the high pressure nozzles 38 are 2 inches apart from each other, the angle off vertical 110 of the discharge stream 108 of the port 104 is about 54 degrees for an intersection at one inch below the surface, and about 9 degrees for an intersection at 6 inches below the surface, and about 5 degrees for an intersection at 12 inches below the surface.

It is contemplated that the ports 104 of the multiport nozzle 102 can be configured such that the discharge streams of termiticide emitted therefrom are generally vertically and that some or all of the plurality of high pressure nozzles 38 can be configured such that the discharge streams of termiticide emitted therefrom are other than vertical. In one suitable embodiment, the termiticide is emitted from the nozzles 38 in a generally conical discharge stream. It is further contemplated that the ports 104 of the multiport nozzle 102 and the plurality of high pressure nozzles 38 can be configured to emit discharge streams of termiticide that are other than vertical. In either of these arrangements, some or all of the plurality of high pressure nozzles 38 can be configured to emit discharge streams that are angled toward the periphery of the control plate (i.e., away from the multiport nozzle 102) to thereby increase the coverage area of the termiticide and that some or all of the plurality of high pressure nozzles 38 can be configured to emit discharge streams that are angled inward and toward the multiport nozzle 102 for intersecting the discharge streams emitted from the ports 104 of the multiport nozzle.

In operation, the manifold head 16 is positioned on the ground and the operator activates the trigger switch 60 causing the discharge valve 56 to open thereby permitting the predetermined quantity of termiticide to flow to and out each of the high pressure nozzles 38 and each of the ports 104 of the multiport high pressure nozzle 102 to thereby injecting termiticide into the ground. The discharge streams 106 of termiticide from each of the high pressure nozzles 38 is injected substantially vertically into the ground. The discharge streams 108 of termiticide from the ports 104 are injected into the ground at an angle off vertical 110 which causes the discharge streams 108 from each of the ports 104 to intersect respective discharge streams 106 from the high pressure nozzles 38 below the surface of the ground.

The angled discharge streams 108 of ports 104 provide for supplying the termiticide to a greater volume of the injection area than just using the high pressure nozzles 38. The angled discharge streams 108 of the ports 104 inject termiticide into the soil within a central injection zone of the injection area, which is located within an outer injection zone defined by the termiticide injected by the high pressure nozzles 38. Injection of termiticide at high pressures causes the soil to fracture as the discharge streams 106, 108 of termiticide pass through the soil. In another embodiment, each of the ports 104 are slightly offset so that their discharge streams 108 of termiticide do not precisely intersect respective discharge streams 106 from the high pressure nozzles 38.

Referring again to FIG. 12, in another embodiment four center high pressure nozzles 112 may be used instead of the multiport nozzle 102. The four center nozzles 112 are collectively positioned in the center of the matrix 100 and are each angled toward a different corner of the square matrix. Similar to the multiport nozzles 102 described above, the center nozzles 112 are configured to direct their discharge streams 108 to intersect a respective discharge stream 106 from one of the high pressure nozzles 38. The intersection of the discharge stream 106 from one of the high pressure nozzle 38 by the discharge stream 108 from one of the center high pressure nozzles 112 may be about 1 inch to about 12 inches below the surface of the soil. The angle off vertical 110 of the discharge stream 108 of the center nozzle 112 is based on the depth of intersection desired and the distance between the high pressure nozzles 38. For example, when high pressure nozzles 38 are 2 inches apart from each other, the angle off vertical 110 of the discharge stream 108 from the center nozzle 112 is about 54 degrees for an intersection at one inch below the surface, and about 9 degrees for an intersection at 6 inches below the surface, and about 5 degrees for an intersection at 12 inches below the surface.

Figure 13:
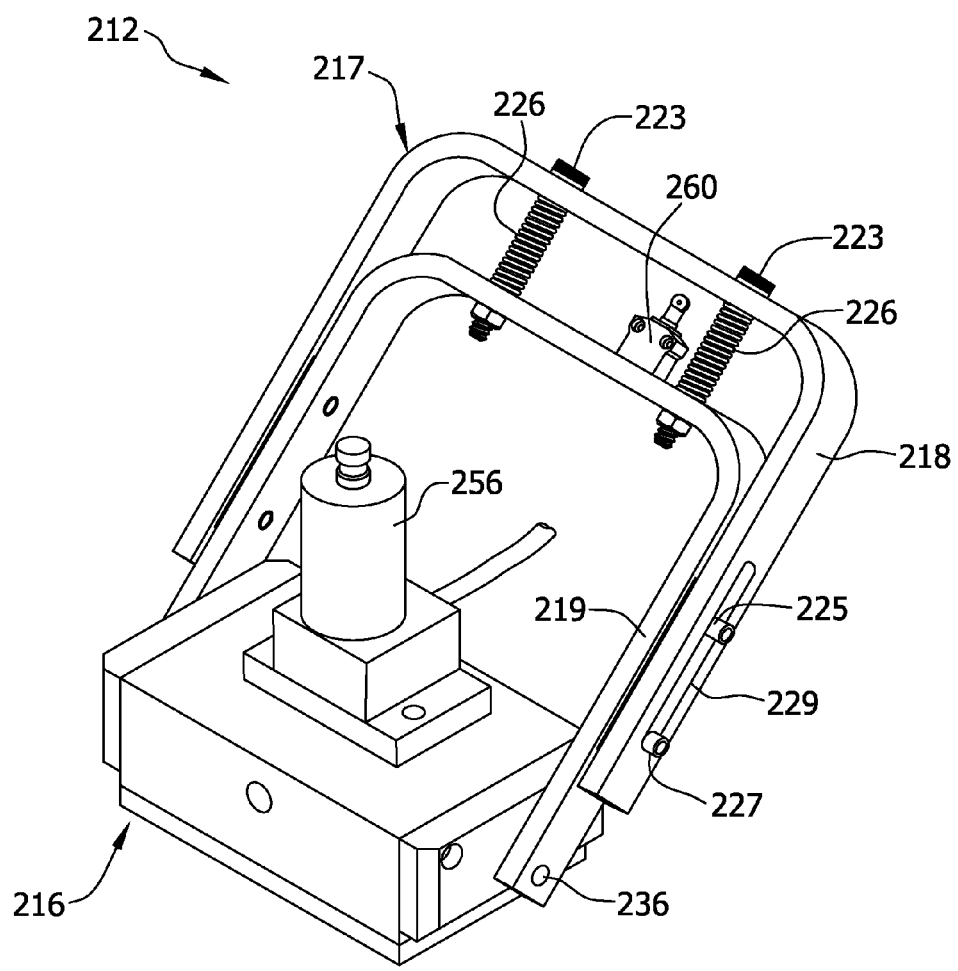
FIG. 13 is a perspective schematic illustration of another embodiment of a handheld application tool.

FIG. 13 is a schematic illustration of another embodiment of a handheld portable application tool 212 (broadly, an "injection apparatus") suitable for use with the high pressure injection system for injecting termiticide into the ground, which was described above. The relative size of the tool 212 makes it suitable for use in tight spaces (e.g., crawl spaces) as well as open spaces (e.g., a lawn). As seen in FIG. 13, the application tool 212 includes a handle 217 and a manifold head 216 mounted to the handle. The manifold head 216, which is pivotally mounted to the handle 217 via a pair of pivot pins 236 (one of the pivot pins being seen in FIGS. 13 and 14), is substantially the same as the manifold head 16 illustrated in FIGS. 1-3. As a result, the manifold head 216 illustrated in FIGS. 13 and 14 will not be described in detail.

Figure 14:
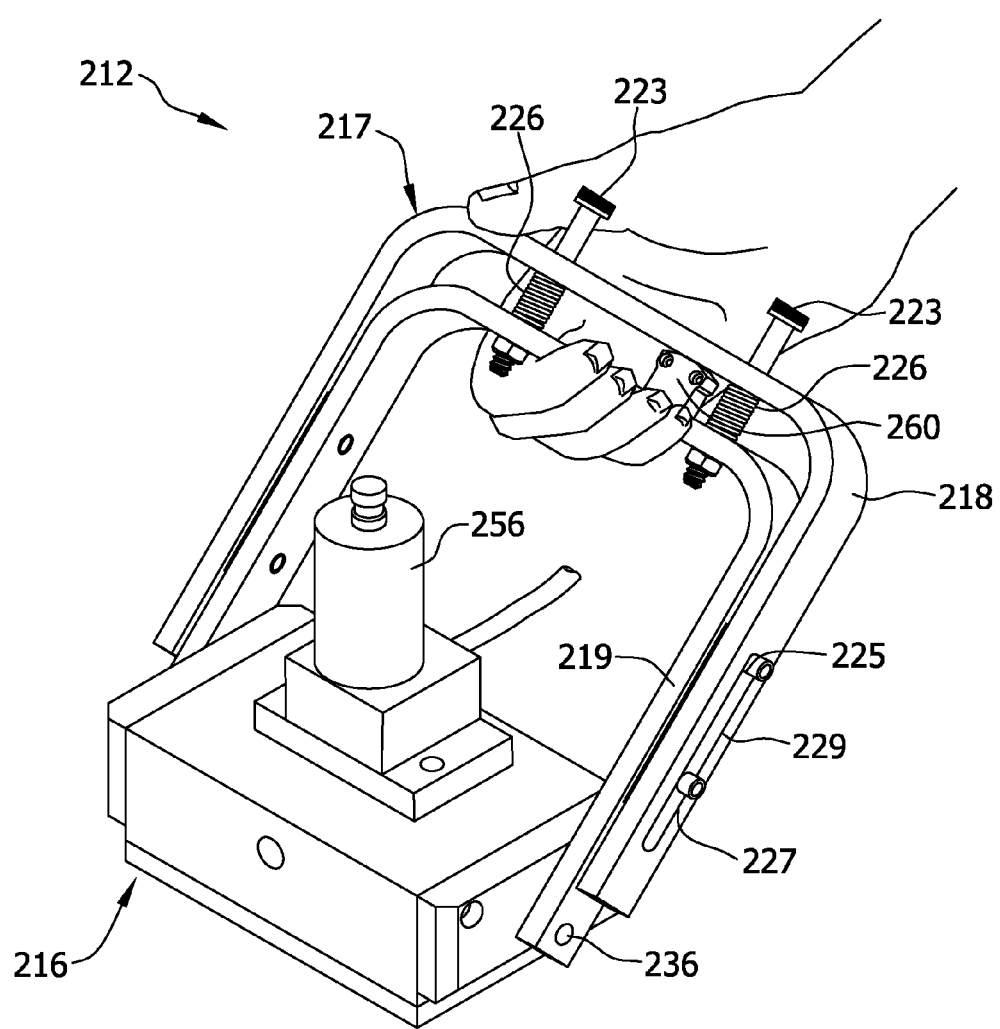
FIG. 14 is a perspective schematic illustration of the handheld application tool of FIG. 13 but with a trigger switch of the tool being actuated.

The handle 217 of the tool 212 includes an upper portion 218 and a lower portion 219. In the illustrated embodiment, both the upper and lower portions 218, 219 of the tool comprise generally U-shaped brackets. The upper portion 218 of the handle 217 can move relative to the lower portion 219 from a first, extended position (FIG. 13) to a second, compressed position (FIG. 14). A biasing element, such as a pair of springs 226, biases the upper portion 218 of the handle 217 toward its first, extended position and away from the lower potion 219. In the illustrated embodiment, each of the springs 226 is mounted on the handle 217 via a bolt 223. In addition, a pair of upper stops 225 and a pair of lower stops 227 are mounted on the lower portion 219 and extend through a slot 229 formed in the upper portion 218 to limit the range of movement of the upper portion relative to the lower portion. One of the upper stops 225 and one of the lower stops 227 are shown in FIGS. 13 and 14. It is understood, however, that any known biasing element 226 may be used and the biasing element can be mounted on the handle 217 in other suitable manners. It is also understood that other types of stops can be used to limit the relative movement between the upper and lower portions 218, 219 of the handle 217.

As illustrated in FIGS. 13 and 14, a trigger switch 260 (broadly, an "actuator") is mounted on the lower portion 219 of the handle 217. The trigger switch 260 is electrically coupled to a discharge valve 256 and activates the discharge valve when the trigger switch is actuated. As seen in FIG. 14, the trigger switch 260 is actuated by the upper portion 218 of the handle 217 being manually pressed into contact with the trigger switch. That is, the trigger switch 260 can be actuated by manually moving the upper portion 218 of the handle 217 from its first, expanded position to its second compressed position by applying a force on the upper portion so that it slides downward relative to the lower portion 219 of the handle until the trigger switch 260 is actuated. Actuation of the trigger switch 260 causes termiticide to be injected into the ground through the manifold 216.

Figure 15:
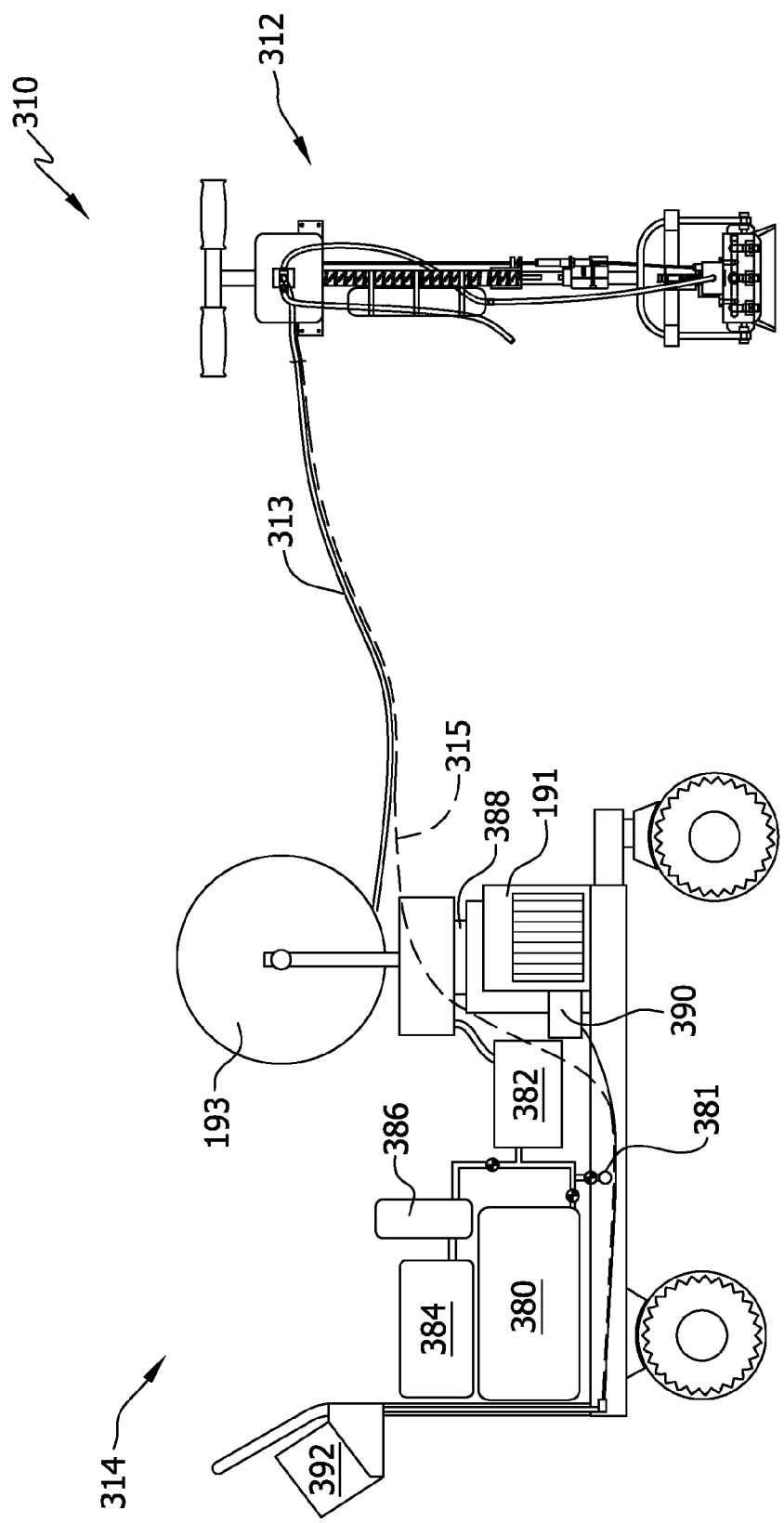
FIG. 15 is a schematic illustration of a high pressure injection system for injecting a termiticide into the ground in accordance with another exemplary embodiment in which the system includes a base unit and a handheld application tool.
Figure 16:
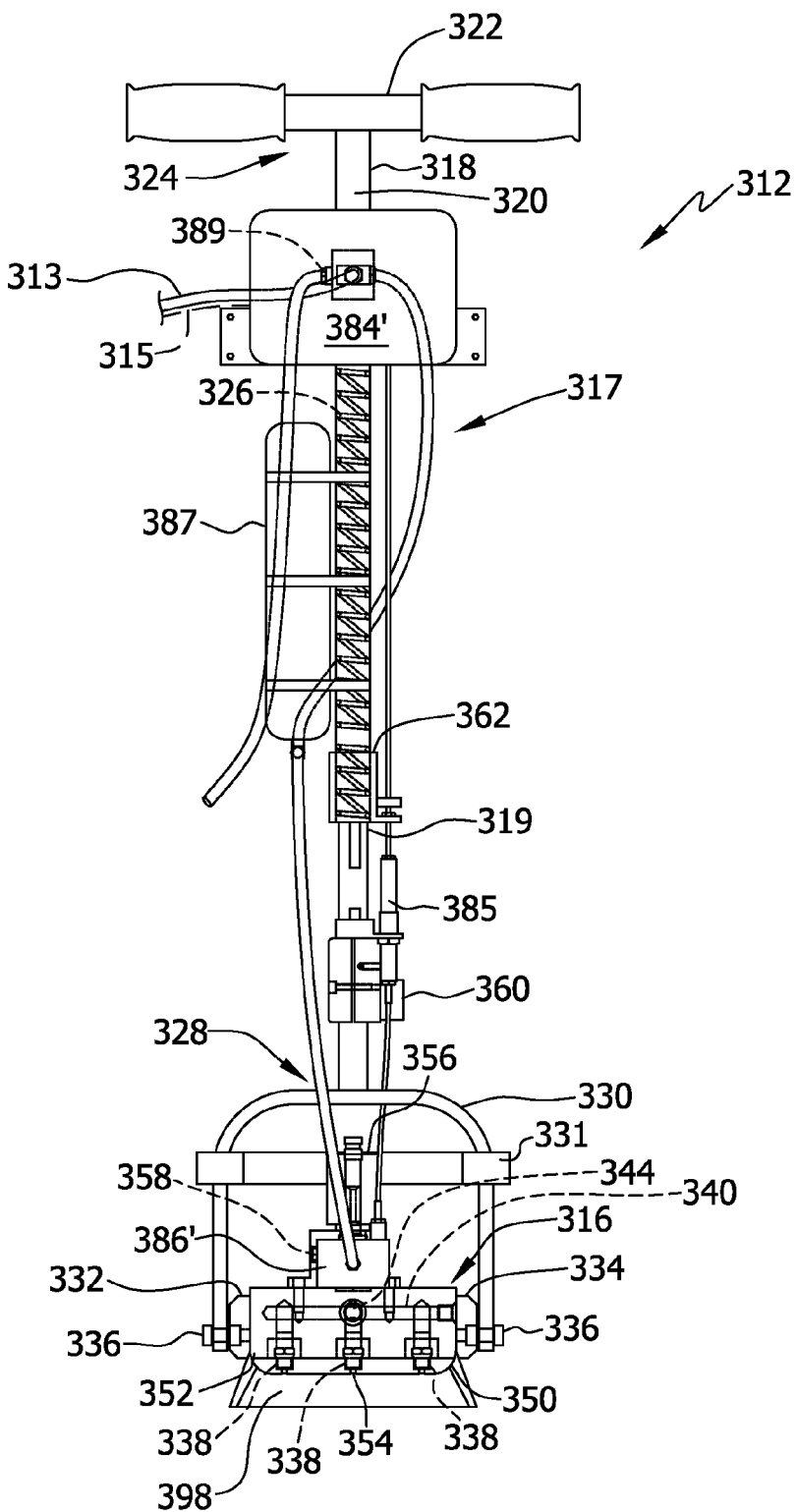
FIG. 16 is a front view schematic illustration of the handheld portable application tool of FIG. 15 with parts cut away.
Figure 17:
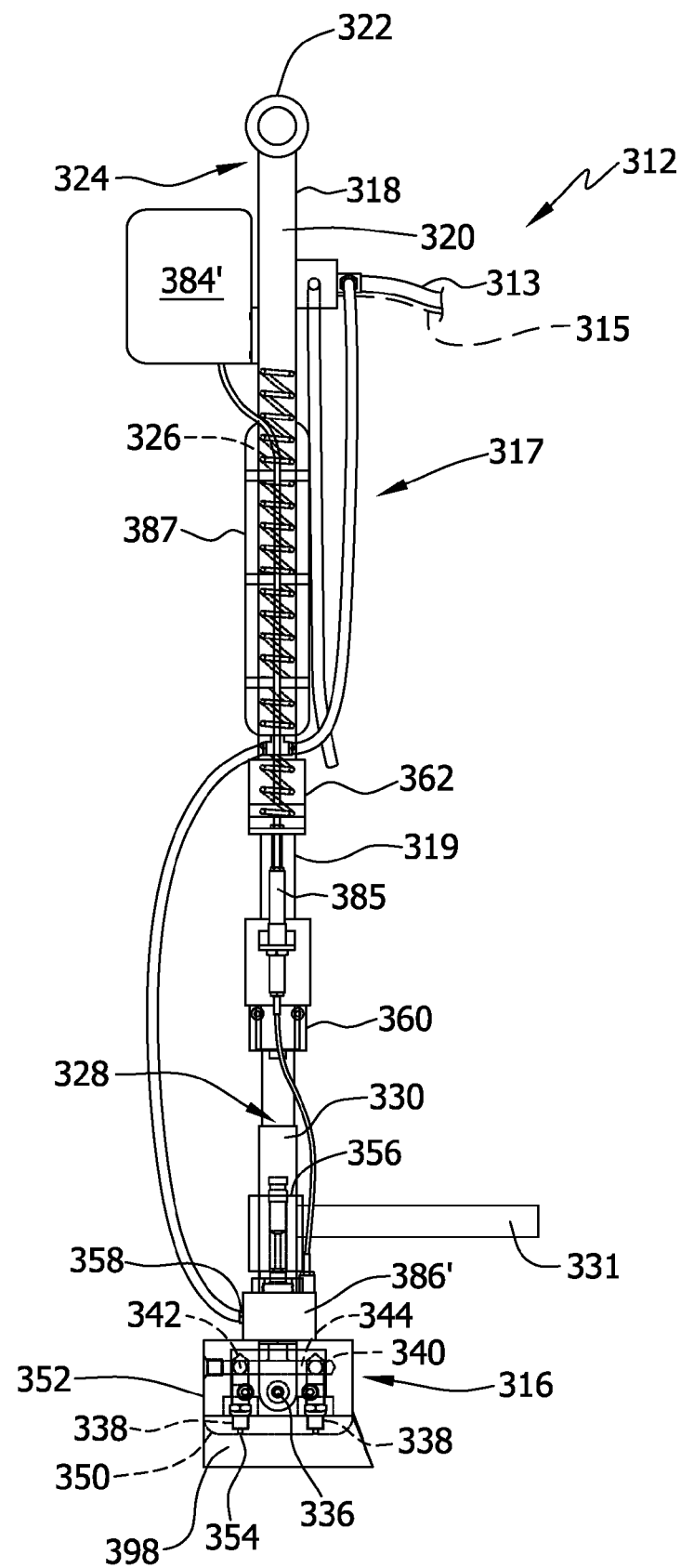
FIG. 17 is a side view schematic illustration of the handheld portable application tool of FIG. 16.

Referring now to FIGS. 15-17, these Figures schematically illustrate a high pressure injection system 310 for injecting termiticide (or other suitable treatment) into the ground in accordance with another exemplary embodiment. As seen in FIG. 15, the injection system 310 includes a handheld portable application tool 312 (broadly, an "injection apparatus") and a supply cart 314 (broadly, a "base unit"). The application tool 312 is connected to the cart 314 via a conduit 313 (e.g., a hose) defining a fluid passageway and at least one electrical connection 315. The conduit 313 permits fluid (e.g., water and/or a termiticide solution) to flow from the cart 314 to the application tool 312. The electrical connection 315 is used for transmitting various control signals between the application tool 312 and the cart 314.

FIG. 16 is a front view schematic illustration of the handheld portable application tool 312, and FIG. 17 is a side view schematic illustration of the application tool 312. The handheld portable application tool 312 includes a handle 317 and a manifold head 316 mounted to the handle. The handle 317 includes an upper portion 318 and a lower portion 319. The upper portion 318 includes a tubular section 320 and a hand grip section 322 attached to an upper end 324 of the tubular section 320. As a result, the upper portion 318 of the handle 317 has a generally T-shape. The lower portion 319 of the handle 317, which is also tubular, is sized for insertion into the tubular section 320 of the upper portion 318 of the handle. With the lower portion 319 of the handle 317 inserted into the tubular section 320 of the upper portion 318 of the handle, the upper portion can move with respect to the lower portion from a first, extended position to a second, compressed position. A biasing element, such as a spring 326, is provided to bias the upper portion 318 of the handle 317 toward its first, extended position. It is understood, however, that any known biasing element 326 may be used. A flange (not shown) or other suitable retainer(s) may be provided to inhibit the lower portion 319 of the handle 317 from being pulled or otherwise withdrawn from the upper portion 318 to thereby ensure that the lower portion remains telescopically attached to the upper portion.

A lower end 328 of lower portion 319 of the handle 317 is attached to an inverted U-shaped attachment bracket 330. The manifold head 316 is pivotally attached at each of its ends 332, 334 to the attachment bracket 330 via a pair of pivot pins 336. It is contemplated that one or more stops (not shown) can be provided to limit the pivoting movement of the handle 317 relative to the manifold 316. Attached to the U-shaped attachment bracket 330 is a foot bracket 331. During use of the tool 312, the user can place one of his/her feet on the foot bracket 331 to inhibit movement of the tool during an injection.

The manifold head 316 includes at least one internal passage to distribute the termiticide to a plurality of high pressure nozzles 338 in fluid communication with the internal passage. As seen in FIG. 17, the illustrated manifold head 316 includes two main internal passages 340, 342, and a cross passage 344 connecting main internal passages. It is contemplated that the manifold head 316 may include any number of high pressure nozzles 338. For example, the manifold head 316 of the exemplary embodiment has a matrix of six high pressure nozzles 338 with each nozzle generally equidistant from each other. Each of the high pressure nozzles 338, in one embodiment, has an orifice diameter ranging from about 0.002 inch to about 0.01 inch.

With reference again to FIG. 16, a contact plate 350 is attached to a bottom surface 352 of the manifold head 316 to protect the high pressure nozzles 338. In the illustrated embodiment, the contact plate 350 includes a plurality of openings 354 with each of the openings being generally aligned with a respective one of the plurality of high pressure nozzles 338. As a result, the high pressure nozzles 338 are spaced from the soil by the contact plate 350 and therefore do not directly contact the soil. Moreover, the contact plate 50 shields or otherwise blocks soil, rocks, and/or other debris that may be "kicked-up" during the injection of the termiticide. As seen in FIG. 17, the contact plate 350 includes rounded edges to facilitate sliding (e.g., dragging) of the tool 312. The contact plate 350 can be made from any suitable material, for example, metal and/or plastic.

In this embodiment, a kick guard 398 extends outward from three sides on the contact plate 350 to further shield or otherwise block soil, rocks, and/or other debris that may be "kicked-up" during the injection of the termiticide. In the illustrated embodiment, one side of the contact plate 350 is free from the kick guard 398 to facilitate placement of the contact plate and manifold head 316 in close proximity to objects and structures. It is understood, however, that the kick guard 398 can extend around the entire periphery (i.e., all four sides) of the contact plate 350. In one suitable embodiment, the kick guard 398 is made from three pieces of suitable rubber material, which each piece of rubber material extending outward from a respective side of the contact plate 350. It is understood, however, that the kick guard 398 can have other suitable configurations (e.g., bristles, strips, flaps) and be made from any suitable material.

As illustrated in FIG. 16, a discharge valve 356 is attached to the manifold head 316 and is in fluid communication with the internal passages 340, 342, 344 in the manifold head and a supply of termiticide. The discharge valve 356 is moveable between an opened position and a closed position. When the discharge valve is in its closed position, termiticide solution is inhibited from flowing to the internal passages 340, 342, 344 in the manifold head via the high pressure inlet port 358. When the discharge valve 356 is opened, the termiticide solution flows into inlet port 358 under high pressure. From the inlet port 358, the pressurized termiticide solution flows into internal passages 340, 342, 344 of the manifold head 316 and through the high pressure nozzles 338 from which the termiticide solution is injected into the ground. In one embodiment, the termiticide solution is pressurized to a pressure of about 25 psi to about 10,000 psi, and in another embodiment, from about 1,000 psi to about 7,000 psi, and in yet another embodiment, at about 4,000 psi.

In one suitable embodiment, the discharge valve 356 is a solenoid operated poppet valve capable of sufficiently rapid operation to allow opening and closing of the discharge valve 356 within the desired time parameters to allow correct depth penetration of the soil based on the pressure in use and correct volume of termiticide solution for the specific application. While it is possible to use a hydraulically actuated valve, the size and weight constraints of such a valve may otherwise limit the utility of the handheld application tool 312.

As illustrated in FIG. 16, a trigger switch 360 (broadly, an "actuator") is mounted on the lower portion 319 of the handle 317 and a trigger switch actuator 362 is mounted on the upper portion 318. The trigger switch 360, which is electrically coupled to the discharge valve 356, activates the discharge valve 356 when the trigger switch actuator 362 engages the trigger switch 360. In the illustrated embodiment and as seen in FIG. 16, the trigger switch actuator 362 is engaged with the trigger switch when the upper portion 318 of the handle 317 is moved to its second, compressed position. Thus, the trigger switch 360 can be actuated by moving the upper portion 318 of the handle 317 from its first, expanded position to its second compressed position by applying a force on the upper portion so that it slides downward relative to the lower portion 319 of the handle until the trigger switch actuator engages the trigger switch 360.

In one suitable embodiment, a kill switch (not shown) can be located on the hand grip section 322 of the upper portion 318 of the handle 317 where it can be actuated by the operator to quickly and easily shut the system 310 off. It is contemplated that the kill switch can be located on other portions of the tool 312 besides the hand grip section 322 of the handle 317. It is also contemplated that a kill switch can be provided on the cart 314 in addition to or instead of the kill switch located on the tool 312.

In this embodiment, a first termiticide concentrate reservoir 384' and a dosing device 385 are mounted on the handle 317 of the tool 312. The dosing device 385 is in fluid communication with termiticide concentrate reservoir 384' and is adapted to deliver a predetermined amount (i.e., a dose) of concentrated termiticide to a suitable first mixing device 386' each time the trigger switch 360 is actuated. In one suitable embodiment, the dosing device 385 is adjustable so that the predetermined amount of concentrated termiticide can be adjusted. In another suitable embodiment, the dosing device 385 is non-adjustable. That is, the amount of concentrated termiticide delivered to the mixing device 386' each time the trigger switch 360 is actuated cannot be changed without replacement of the dosing device. One suitable dosing device 385 is available from SMC Corporation of America of Indianapolis, Ind. as part no. NCMB075-0125. In the illustrated embodiment, the mixing device 386' is mounted on top of the manifold head 316 but it is understood that the mixing device can be otherwise mounted. For example, the mixing device 386' can be mounted on the lower portion 319 of the handle 317.

With reference still to FIG. 16, a pressure accumulator 387 is mounted to the handle 317. The pressure accumulator 387 is adapted to store pressurized water from the cart 314 prior to it being delivered to the mixing device 386'. The pressure accumulator 387 minimizes the effect of the pressure drop between the cart 314 to the mixing device 386'. Thus, the pressure accumulator 387 provides pressurized water from the cart 314 to the mixing device 386' at a higher pressure than if the pressurized water was delivered directly to the mixing device from the cart.

In the embodiment illustrated in FIG. 15, the cart 314 includes a water reservoir 380, a high pressure pump 382, a second termiticide concentrate reservoir 384, and a second mixing device 386 that is capable of supplying the appropriate amount of termiticide concentrate to be mixed with the appropriate amount of water to form the termiticide solution. A water inlet 381 for receiving water from an external water source (e.g., a standard residential water spigot) is also provided. It is contemplated that either the water reservoir 380 or the water inlet 381 can be omitted.

The supply cart 314 also includes a gasoline engine 388 with a generator 390 for generating power for operating the pressure pump 382 and generating electrical current for operating a controller 392 associated with the system 310. In another embodiment, electrical power can be supplied by connecting into an electrical outlet located at the application site. A radiator 191 is provided to cool the pressurized water being driven by the high pressure pump 382. In the illustrated embodiment, a hose reel 193 is mounted on the cart 314 for winding the hose 313 that extends between the cart 314 and the application tool 312. A pressurized water bypass 389 is provided on the handle 317 of the tool 312 for allowing pressurized water to discharged prior to the pressure accumulator 387. The bypass 389 can be used to facilitate priming of the high pressure pump 382 and flushing termiticide solution from the hose 313.

The controller 392 permits the operator of the system 310 to selectively set a pulse duration and pressure level for termiticide injections. The controller 392 may be programmable to permit the operator to enter parameters associated with a particular manifold head 316 in use, such as by defining the number of orifices and their sizes, parameters with a termiticide solution in use, such that dosing through the mixing device 386 can be properly controlled, or the number of injections can be tracked, and the like.

To inject the termiticide into the ground, the operator positions handheld portable application tool 312 such that the contact plate 350 is in contact with the surface of the ground. A downward force between about 15 to 20 pounds is applied by the operator to the upper portion 318 of the handle 317 to move the upper portion 318 from its first position to its second position and thereby cause the trigger switch actuator 362, which is mounted to the upper portion, to engage the trigger switch 360, which is mounted to the lower portion 319. Engagement of the trigger switch actuator 362 and the trigger switch 360 actuates the discharge valve 356. More specifically, an electronic signal is sent from the trigger switch 360 to the discharge valve 356 causing the discharge valve to move from its closed position to its opened position for a predetermined amount of time.

In addition, movement of the upper portion 318 of the handle 317 relative to the lower portion 319 causes a predetermined amount of termiticide concentrate to be delivered by the dosing device 385 from the first termiticite concentrate reservoir 384' to the mixing device 386'. Opening the discharge valve 356 causes the pressure accumulator 387 to release at least a portion of the pressurized water stored therein to the mixing device 386'. The termiticite concentration and pressurized water mix within the mixing device 386' to form a termiticide solution. The termiticide solution is then driven to the manifold head 316 where it flows to and out the high pressure nozzles 338 for injection into the ground.

The operator then releases the pressure from the handle 317, which resets the trigger switch 360, the dosing device 385, and the pressure accumulator 387. More specifically, the spring 326 causes the upper portion 318 of the handle 317 to move back to its first, extended position. The illustrated trigger switch 360 is configured to work only once during each compression of handle 317 to prevent repeated opening of the discharge valve 356 until the handle 317 has been reset.

The depth of penetration of the termiticide solution into the ground is a function of the pressure at which the termiticide solution is discharged from the tool 312 and the type of soil into which the termiticide is discharged. In one suitable embodiment, the penetration of termiticide into the ground is between about 12 to 16 inches.

The second termiticide concentrate reservoir 384 and the second mixing device 386, which are mounted on the cart 314, allow the cart to be used for low pressure applications. Low pressure applications of termiticide can be carried out using the application tool 312 illustrated herein or using conventional rodding techniques. It is understood that the second termiticide concentrate reservoir 384 and the second mixing device 386 can be omitted.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of treating soil adjacent a structure, said method comprising:
   positioning an injection apparatus over a first injection site generally adjacent a structure, the injection apparatus including a manifold head having an internal passage, a plurality of nozzles coupled to the manifold head in fluid communication with the internal passage, and a flat contact plate having a matrix of openings arranged such that at least two of the openings are spaced from each other both longitudinally and transversely with respect to the contact plate, each opening aligned with one of the respective nozzles;
   injecting pesticide down into the soil at said first injection site using the injection apparatus, said injecting step being performed without penetration of the soil by the injection apparatus at said first injection site;

moving the injection apparatus over a second injection site at least in part different from said first injection site and generally adjacent the structure, the injection of pesticide into the soil being ceased while moving the injection apparatus from the first injection site to the second injection site; and injecting pesticide down into the soil at said second injection site using the injection apparatus, said injecting step being performed without penetration of the soil by the injection apparatus at said second injection site.

2. The method of claim 1 wherein the step of positioning the injection apparatus over a first injection site comprises positioning the injection apparatus in contact with the ground surface over the first injection site, the step of positioning the injection apparatus over a second injection site comprising positioning the injection apparatus in contact with the ground surface over the second injection site.

3. The method of claim 1 further comprising moving the injection apparatus to a plurality of additional injection sites at least in part different from each other and adjacent the structure generally about at least a portion of a perimeter of the structure; and injecting pesticide down into the soil at each additional injection site using the injection apparatus at each respective additional injection site.

4. The method of claim 3 wherein the first injection site, the second injection site and plurality of additional injection sites are disposed about substantially the entire perimeter of the structure.

5. The method of claim 4 wherein the first injection site, the second injection site and plurality of additional injection sites are disposed in generally side-by-side relationship with each other in spaced relationship with the structure.

6. The method of claim 1 wherein the method is for treating against insects, the steps of injecting pesticide at the first and second injection sites comprising injecting insecticide down into the soil at the respective first and second injection sites.

7. The method of claim 6 wherein the treatment method is for treating against insects, the steps of injecting insecticide at the first and second injection sites comprising injecting termiticide down into the soil at the respective first and second injection sites.

8. The method of claim 1 wherein the steps of injecting pesticide at the first and second injection sites comprise injecting pesticide generally vertically down into the soil at the respective first and second injection sites.

9. The method of claim 1 wherein the steps of injecting pesticide at the first and second injection sites comprise injecting pesticide down into the soil other than vertically.

10. The method of claim 1 wherein the steps of injecting pesticide comprise using the injection apparatus to deliver a plurality of discrete streams of pesticide down into the soil at each of said first and second soil injection sites.

11. The method of claim 10 wherein at each of said first and second soil injection sites, the injection apparatus is used to deliver at least one discrete stream of pesticide generally vertically down into the soil and at least one other discrete stream of pesticide down into the soil other than vertically.

12. The method of claim 1 further comprising the step of visibly marking the location of the first injection site, said marking step being performed one of concurrently with and after injecting pesticide down into the soil at the first injection site.

13. The method of claim 1 further comprising the step of delivering pesticide onto the ground surface at least at one of the first and second injection sites.

14. The method of claim 13 wherein the delivery step is performed concurrently with injecting pesticide down into the soil.

15. The method of claim 13 where the delivery step comprises operating the injection apparatus to deliver pesticide onto the ground surface.

16. The treatment method of claim 1 wherein the structure comprises one of a building structure, a tree, a fence, a post, a pole, and a plant.

17. The method of claim 1 wherein the step of injecting the pesticide down into the soil at the first injection site comprises actuating an actuator to cause a discharge valve to move from a closed position wherein the pesticide is inhibited from flowing from the injection apparatus to an opened position wherein pesticide flows from the injection apparatus for injection of the pesticide down into the soil, the actuator operating to maintain the valve open for a predetermined injection period after which the actuator causes the discharge valve to move back to its closed position for movement of the apparatus to the second injection site.

18. The method of claim 1 wherein the step of injecting the pesticide down into the soil at the first injection site comprises placing a contact plate of the injection apparatus into contact with the soil and injecting pesticide through the contact plate and down into the soil, the step of moving the injection apparatus over a second injection site comprising lifting the contact plate out of contact with the soil at the first injection site and placing the contact plate down into contact with the soil over the second injection site.

19. A method of treating soil adjacent a structure, the method comprising:

positioning a head of an injection apparatus generally flat against the soil to be injected with pesticide, the head including a plurality of first high pressure nozzles, at least one second high pressure nozzle, and a contact plate coupled to a bottom surface of the head, the contact plate having a plurality of first exit orifices, each first exit orifice corresponding to a respective one of said first high pressure nozzles and a second exit orifice corresponding to said at least one second high pressure nozzle;

delivering a pesticide solution to the plurality of first high pressure nozzles and the at least one second high pressure nozzle;

injecting the pesticide solution into the soil defining an outer injection zone by permitting the pesticide solution to flow through the plurality of first high pressure nozzles and exit the head through the corresponding first exit orifices into the soil without prior disturbance of the soil, the plurality of first exit orifices arranged in a matrix such that at least two of the openings are spaced both longitudinally and transversely from each other with respect to the contact plate; and injecting the pesticide solution into the soil defining a central injection zone by permitting the pesticide solution to flow through the at least one second high pressure nozzle and exit the head through the corresponding second exit orifice into the soil without prior disturbance of the soil, the central injection zone being disposed within the outer injection zone.

20. The method as set forth in claim 19 wherein the pesticide solution is injected into the soil at a pressure between about 50 psi and about 10,000 psi.

21. The method as set forth in claim 20 wherein the pesticide solution is injected into the soil at a pressure between about 1,000 psi and about 7,000 psi.

22. The method as set forth in claim 21 wherein the pesticide solution is injected into the soil at a pressure of 4,000 psi.

23. The method as set forth in claim 19 wherein the pesticide solution is injected into the soil to a depth between about 2 inches and 14 inches.

24. The method as set forth in claim 23 wherein the pesticide solution is injected into the soil to a depth between about 5 inches and 9 inches.

25. The method as set forth in claim 19 wherein the pesticide solution is injected into the soil to a depth of about 6 inches.

26. The method as set forth in claim 19 further comprising depositing a marking material onto the soil to indicate an area in which the pesticide solution has been injected.

27. The method as set forth in claim 26 wherein depositing a marking material comprises depositing a marking material onto the soil at approximately the same time as injecting the pesticide solution into the soil.

28. The method as set forth in claim 19 wherein the injection apparatus includes at least one low pressure nozzle, the method further comprises depositing the pesticide solution onto the soil by permitting the pesticide solution to flow through the at least one low pressure nozzle and onto the soil at a pressure of less than about 30 psi.

29. The method as set forth in claim 19 wherein injecting the pesticide solution into the soil comprises injecting an insecticide solution.

30. The method as set forth in claim 19 wherein injecting an insecticide solution comprises injecting a termiticide solution.

31. The method as set forth in claim 19 wherein injecting the pesticide solution into the soil comprises injecting a measured dose of the pesticide solution into the soil.

32. The method as set forth in claim 19 further comprising moving the injection apparatus to a next application point.

33. The method as set forth in claim 19 further comprising mixing a pesticide concentrate with water using a mixing device to form the pesticide solution.

34. A method of treating soil adjacent a structure, the method comprising:
positioning an injection apparatus against the soil, the injection apparatus having a manifold head including a plurality of high pressure nozzles and a plurality of low pressure nozzles coupled to the manifold head and positioned adjacent to the soil, the manifold head having a contact member coupled thereto and including a plurality of first openings in fluid communication with the plurality of high pressure nozzles, the plurality of first openings arranged such that at least two of the openings are spaced from each other both longitudinally and transversely with respect to the contact plate, and a plurality of second openings in fluid communication with the plurality of low pressure nozzles, the plurality of second openings arranged such that at least two of the openings are spaced from each other both longitudinally and transversely with respect to the contact plate;
delivering a pesticide solution to the plurality of high pressure nozzles and the plurality of low pressure nozzles;
injecting the pesticide solution into the soil by permitting the pesticide solution to flow through the plurality of high pressure nozzles and into the soil without prior disturbance of the soil; and
applying the pesticide solution on the soil by permitting the pesticide solution to flow through the plurality of low pressure nozzles and onto the soil.

35. The method as set forth in claim 34 wherein the pesticide solution is injected into the soil through the plurality of high pressure nozzles at a pressure between about 50 psi and about 10,000 psi.

36. The method as set forth in claim 35 wherein the pesticide solution is injected into the soil through the plurality of high pressure nozzles at a pressure between about 1,000 psi and about 7,000 psi.

37. The method as set forth in claim 36 wherein the pesticide solution is injected into the soil through the plurality of high pressure nozzles at a pressure of 4,000 psi.

38. The method as set forth in claim 34 wherein the pesticide solution is injected into the soil to a depth between about 2 inches and 14 inches.

39. The method as set forth in claim 38 wherein the pesticide solution is injected into the soil to a depth between about 5 inches and 9 inches.

40. The method as set forth in claim 39 wherein the pesticide solution is injection into the soil to a depth of about 6 inches.

41. The method as set forth in claim 34 wherein the pesticide solution is applied to the soil through the plurality of low pressure nozzles at a pressure of less than about 30 psi.

42. The method as set forth in claim 34 wherein injecting the pesticide solution into the soil comprises injecting an insecticide solution.

43. The method as set forth in claim 42 wherein injecting an insecticide solution comprises injecting a termiticide solution.

44. The method as set forth in claim 34 further comprising actuating a single trigger switch to inject the pesticide solution into the soil and to apply the pesticide solution to the soil.

45. The method as set forth in claim 44 where the pesticide solution is injected into the soil and applied to the soil at approximately the same time.

46. A method of treating soil adjacent a structure, said method comprising:
positioning a contact plate of an injection apparatus generally flat against a first injection site generally adjacent a structure, the injection apparatus having a manifold head and at least one first high pressure nozzle configured to emit a first discrete stream and at least one second high pressure nozzle configured to emit a second discrete stream coupled to the manifold head, the contact plate being coupled to the manifold head and having a first opening associated with the at least one first high pressure nozzle and a second opening associated with the at least one second high pressure nozzle, the first opening and the second opening arranged such that they are spaced from each other both longitudinally and transversely with respect to the contact plate;
injecting pesticide down into the soil at said first injection site other than perpendicular to the contact plate using the injection apparatus, the first discrete stream being emitted in a first direction and the second discrete stream being emitted in a second direction that is angled relative to the first direction, said injecting step being performed without prior penetration of the soil at said first injection site;
moving the injection apparatus to position the contact plate generally flat against a second injection site at least in part different from said first injection site and generally adjacent the structure; and
injecting pesticide down into the soil at said second injection site other than perpendicular to the contact plate using the injection apparatus, the first discrete stream being emitted in a first direction and the second discrete stream being emitted in a second direction that is angled relative to the first direction, said injecting step being performed without prior penetration of the soil at said second injection site.

47. The method of claim 46 further comprising operating the injection apparatus to inject pesticide down into the soil at the respective first and second injection sites generally perpendicular to the contact plate.

48. The method of claim 46 wherein the first discrete stream is injected generally vertically down and the second discrete stream is injected other than vertically down, the second discrete stream of pesticide being angled generally toward the first discrete stream of pesticide.

49. The method of claim 48 wherein the second discrete stream of pesticide is angled to intersect the first discrete stream of pesticide.

50. The method of claim 49 wherein the second discrete stream of pesticide is angled to intersect the first discrete stream of pesticide at a predetermined depth.

51. The method of claim 50 wherein the second discrete stream of pesticide is angled to intersect the first discrete stream of pesticide at a depth of about 6 inches.

52. The method of claim 46 wherein operating the injection apparatus comprises operating the injection apparatus to deliver a plurality of discrete streams of pesticide other than vertically down into the soil at each of the first and second soil injection sites.

53. The method of claim 46 further comprising visibly marking the location of the first injection site, said marking step being performed one of concurrently with and after operating the injection apparatus to inject pesticide into the soil at the first injection site.

\* \* \* \* \*